United States Patent
Oda

(10) Patent No.: US 9,282,943 B2
(45) Date of Patent: Mar. 15, 2016

(54) RADIOGRAPHIC IMAGING DEVICE, METHOD OF CONTROLLING RADIATION DETECTION SENSITIVITY AND PROGRAM STORAGE MEDIUM

(71) Applicant: FUJIFILM CORPORATION, Tokyo (JP)

(72) Inventor: Yasufumi Oda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 199 days.

(21) Appl. No.: 13/940,027

(22) Filed: Jul. 11, 2013

(65) Prior Publication Data

US 2014/0016749 A1   Jan. 16, 2014

(30) Foreign Application Priority Data

Jul. 13, 2012 (JP) .................. 2012-158113

(51) Int. Cl.
*H05G 1/56* (2006.01)
*H01L 27/146* (2006.01)
(Continued)

(52) U.S. Cl.
CPC ............... *A61B 6/5258* (2013.01); *A61B 6/585* (2013.01); *H04N 5/357* (2013.01); *A61B 6/548* (2013.01); *G01T 1/247* (2013.01); *H01L 27/14658* (2013.01); *H04N 5/32* (2013.01); *H04N 5/365* (2013.01); *H05G 1/30* (2013.01); *H05G 1/56* (2013.01)

(58) Field of Classification Search
CPC ........ A61B 6/52; A61B 6/5258; A61B 6/582; A61B 6/585; G01N 23/00; G01N 23/02; G01N 23/04; G01N 23/06; G01N 23/08; G01N 23/083; G01T 1/00; G01T 1/02; G01T 1/023; G01T 1/026; G01T 1/16; G01T 1/1603; G01T 1/1606; G01T 1/17; G01T 1/171; G01T 1/20; G01T 1/2006; G01T 1/208; G01T 1/24; G01T 1/246; G01T 1/247; H01L 31/00; H01L 31/02; H01L 31/02016; H01L 27/14; H01L 27/144; H01L 27/146; H01L 27/14601; H01L 27/14609; H01L 27/14612; H01L 27/14638; H01L 27/14643; H01L 27/14658; H01L 27/14676; H01L 27/148; H01L 27/14806; H01L 27/14812; H05G 1/00; H05G 1/02; H05G 1/08; H05G 1/26; H05G 1/265; H05G 1/28; H05G 1/30; H05G 1/38; H05G 1/42; H05G 1/44; H05G 1/56; H04N 1/357; H04N 1/3577; H04N 1/361; H04N 1/363; H04N 1/365
USPC ............... 378/19, 91, 96, 114, 162, 165, 189, 378/204, 207, 210, 901; 250/252.1, 370.01, 250/370.08, 370.09, 370.11, 370.14, 371, 250/394, 395; 348/180, 192, 193, 241, 470, 348/533
See application file for complete search history.

(56) References Cited

U.S. PATENT DOCUMENTS 6,453,008 B1 * 9/2002 Sakaguchi et al. ............ 378/98.7
8,637,832 B2 * 1/2014 Watanabe et al. ............. 250/394
(Continued)

FOREIGN PATENT DOCUMENTS

JP   2008-271049 A   11/2008
JP   2009-212389 A   9/2009
(Continued)

OTHER PUBLICATIONS

Japanese Office Action, dated Dec. 8, 2015, issued in corresponding Japanese Patent Application No. 2012-158113 (with translation).

*Primary Examiner* — Anastasia Midkiff
(74) *Attorney, Agent, or Firm* — Birch, Stewart, Kolasch & Birch, LLP

(57) ABSTRACT

A radiographic imaging device including: a sensor portion that generates an output signal according to an irradiated amount of irradiated radiation; a detector that based on the output signal detects a radiation irradiation start of radiation irradiated from a radiation source during capture of a radiographic image; a noise data generation means that, based on an output signal from the sensor portion in a non-irradiation state of radiation from the radiation source, generates noise data relating to noise incorporated in the output signal; a controller that controls detection sensitivity to radiation irradiation start in the detector according to a degree of variation in noise level expressed by the noise data; and an imaging unit that captures the radiographic image after radiation irradiation start has been detected by the detector.

5 Claims, 21 Drawing Sheets

(51) Int. Cl.

| | | |
|---|---|---|
| *G01T 1/24* | (2006.01) | |
| *H04N 5/32* | (2006.01) | |
| *A61B 6/00* | (2006.01) | |
| *H04N 5/357* | (2011.01) | |
| *H04N 5/365* | (2011.01) | |
| *H05G 1/30* | (2006.01) | |

(56) References Cited

U.S. PATENT DOCUMENTS

| | | | |
|---|---|---|---|
| 8,785,863 B2* | 7/2014 | Oda | 250/366 |
| 2008/0259197 A1 | 10/2008 | Ito et al. | |
| 2009/0224235 A1 | 9/2009 | Kitamura et al. | |
| 2012/0097860 A1* | 4/2012 | Oguma | 250/394 |
| 2012/0132821 A1* | 5/2012 | Kuwabara | 250/370.08 |
| 2012/0189098 A1* | 7/2012 | Liu et al. | 378/62 |
| 2012/0199751 A1* | 8/2012 | Watanabe | 250/370.09 |
| 2012/0242871 A1* | 9/2012 | Iwashita et al. | 348/241 |
| 2012/0288061 A1* | 11/2012 | Okada | 378/62 |

FOREIGN PATENT DOCUMENTS

| | | |
|---|---|---|
| JP | 2011-177356 A | 9/2011 |
| JP | 2011-185622 A | 9/2011 |
| JP | 2011-193306 A | 9/2011 |
| JP | 2012-115306 A | 6/2012 |

\* cited by examiner

PLEASE ENTER SUBJECT NAME,
IMAGING TARGET SITE, IMAGING POSTURE
AND EXPOSURE CONDITIONS

NAME

IMAGING
TARGET SITE

IMAGING
POSTURE

EXPOSURE     TUBE
CONDITIONS   CURRENT

TUBE
             VOLTAGE

EXPOSURE
             DURATION

INPUT
COMPLETE

FIG.20

| STANDARD DEVIATION | SWITCH DRIVE STATE |
|---|---|
| $\sim \sigma_1$ | SWITCH 92D: OFF<br>SWITCH 92F: OFF |
| $\sigma_2 \sim \sigma_3$ | SWITCH 92D: ON<br>SWITCH 92F: OFF |
| $\sigma_4 \sim$ | SWITCH 92D: ON<br>SWITCH 92F: ON |

$\sigma_1 < \sigma_2 < \sigma_3 < \sigma_4$

FIG.22

| STANDARD DEVIATION | CHARGE ACCUMULATION DURATION |
|---|---|
| $\sim \sigma_1$ | $T_1$ |
| $\sigma_2 \sim \sigma_3$ | $T_2$ |
| $\sigma_4 \sim$ | $T_3$ |

$\sigma_1 < \sigma_2 < \sigma_3 < \sigma_4$  $T_1 < T_2 < T_3$

RADIOGRAPHIC IMAGING DEVICE, METHOD OF CONTROLLING RADIATION DETECTION SENSITIVITY AND PROGRAM STORAGE MEDIUM

CROSS-REFERENCE TO RELATED APPLICATION

This application claims priority under 35 USC 119 from Japanese Patent Application No. 2012-158113 filed on Jul. 13, 2012, the disclosure of which is incorporated by reference herein.

BACKGROUND OF THE INVENTION

1. Field of the Invention

The present invention relates to a radiographic imaging device that captures a radiographic image expressing radiation that has passed through an imaging subject, a method of controlling detection sensitivity to radiation irradiation start and a storage medium stored with a program.

2. Description of the Related Art

Recently, radiation detectors such as Flat Panel Detectors (FPDs) are being implemented in which a radiation sensitive layer is disposed on a Thin Film Transistor (TFT) active matrix substrate and with which radiation can be converted directly into digital data. Radiographic imaging devices such as electronic cassettes that employ such radiation detectors to capture radiographic images expressing irradiated radiation are also being implemented. Conversion methods for converting radiation into electric signals used by such radiation detectors include for example indirect conversion methods, in which radiation is first converted into light with a scintillator and then the converted light is converted into charge by a photodiode, or direct conversion methods in which radiation is converted into charge with a semiconductor layer containing for example amorphous selenium. There are various materials that may be used in the semiconductor layer for each method.

In radiographic imaging devices equipped with FPDs, it is necessary to perform synchronization control between the FPD and a radiation source in order to match the start of an accumulation operation, in which the FPD accumulates signal charge, to an irradiation timing of irradiation of radiation from the radiation source. In order to synchronize the timing for the start of radiation irradiation and the timing for the start of the accumulation operation of signal charge by the FPD, a controller such as a console that controls the radiographic imaging device receives an irradiation start signal generated by an irradiation switch connected to the radiation source and supplies this signal to the radiographic imaging device as a synchronization signal. The radiographic imaging device transitions to the accumulation operation and starts imaging on receipt of this synchronization signal.

However, in cases where an imaging system is configured including a radiographic imaging device and a radiation source, sometimes a synchronization control interface installed as standard in the radiographic imaging device or the console thereof (for example cable or connector standards, synchronization signal format) is not compatible with an interface of the radiation source. Due to such issues, radiographic imaging devices are being developed that include an automatic radiation detection function, with radiation irradiation start automatically detected by the radiographic imaging device itself, without the use of a synchronization signal.

For example, Japanese Patent Application Laid-Open (JP-A) No. 2011-185622 discloses a radiographic imaging device provided with: plural radiation detection elements arrayed in a 2D formation in each region of regions partitioned by plural scan lines and plural signal lines; current detection means that detects current flowing in a bias line for applying a bias voltage to the radiation detection elements; control means that detects radiation irradiation start based on a value of the current detected by the current detection means; and memory pre-stored with change profiles of the current detected by the current detection means during reset processing of each of the radiation detection elements. The control means detects radiation irradiation start based on a value $\Delta V$ that is the value of the current detected by the current detection means during the reset processing of each of the radiation detection elements reduced by a value corresponding to a value of the current in the change profile.

Moreover, JP-A No. 2011-193306 discloses technology in which, at a point in time when radiation is definitely not being irradiated in a radiographic imaging device, acquiring image data d (offset correction value O) and an integrated value $\Sigma d(n)$ or a summed value $\Sigma d(m)$ for each image data d from each of radiation detection elements 7, or acquiring an integrated value $\Sigma d(n)$ or summed value $\Sigma d(m)$ for plural frames' worth of image data d and computing average values thereof. A threshold value for detecting radiation irradiation start each time radiographic imaging is performed by is then set by increasing these values by adding a specific value.

In a radiographic imaging device (referred to below as an electronic cassette) with an automatic radiation detection function such as disclosed in JP-A No. 2011-185622, there is an issue of false detection of radiation irradiation start due to noise that has been incorporated into the radiation detection system. Conceivable noise sources are, for example, dark charge occurring inside the electronic cassette, magnetic fields and electromagnetic waves emitted from external devices such as Magnetic Resonance Imaging (MRI) devices, and noise caused externally for example by vibration of a table on which the electronic cassette is installed. Of such noises, the noise generation state from noise sources present inside the electronic cassette, such as dark charge, is not expected to fluctuate greatly. Namely, the amplitude fluctuation of noise occurring inside the electronic cassette is expected to be comparatively small, leading to comparatively little variation in noise level. It is accordingly possible to avoid the above false detection by providing a fixed margin to a threshold value for determination of radiation irradiation start.

However, it is foreseen that the level of noise incorporated into the radiation detection system of the electronic cassette from noise sources external to the electronic cassette, for example electromagnetic waves emitted from external devices and vibration, will fluctuate greatly depending on such factors as where the electronic cassette is installed and the time of day. Namely, the amplitude fluctuation of external noise caused by external factors is expected to be comparatively large, with comparatively large variation in the noise level. Accordingly, when the electronic cassette is installed in a noisy environment that is affected by external noise sources, it is foreseen that even if a fixed margin is provided to a threshold value for determination of radiation irradiation start, noise will still occur at a level that exceeds the margin amount. Such cases lead to the false detection of radiation irradiation start. There is therefore the concern of frequent false detection of radiation irradiation start due to noise when the electronic cassette is installed in a noisy environment affected by external noise sources, with the results that the transition to an accumulation operation cannot be made at an appropriate timing, and that radiographic imaging cannot be appropriately performed.

Moreover, even when as disclosed in JP-A No. 2011-193306, at a point in time when radiation is definitely not being irradiated in a radiographic imaging device, image data d and an integrated value Σd(n) or a summed value Σd(m) for each image data d is acquired, average values thereof are computed, and a threshold value for the detection of radiation irradiation start is set by then adding a specific value to these computed values, it is foreseeable that there will be large fluctuations in the noise level after the threshold value has been set, in which case there is still a concern of false detection of radiation irradiation start.

SUMMARY

An aspect of the present invention provides a radiographic imaging device that includes: a sensor portion that generates an output signal according to an irradiated amount of irradiated radiation; a detector that based on the output signal detects a radiation irradiation start of radiation irradiated from a radiation source during capture of a radiographic image; a noise data generator that, based on an output signal from the sensor portion in a non-irradiation state of radiation from the radiation source, generates noise data relating to noise incorporated in the output signal; a controller that controls detection sensitivity to radiation irradiation start in the detector according to a degree of variation in noise level expressed by the noise data; and an imaging unit that captures the radiographic image after radiation irradiation start has been detected by the detector.

BRIEF DESCRIPTION OF THE DRAWINGS

Exemplary embodiments of the present invention will be described in detail based on the following figures, wherein:

FIG. 14 is a schematic diagram illustrating an example of an initial information input screen according to an exemplary embodiment of the present invention;

FIG. 20 is a diagram illustrating a reference table used in processing in a second signal processor according to the second exemplary embodiment of the present invention;

FIG. 22 is a diagram illustrating a reference table used in processing in a second signal processor according to the third exemplary embodiment of the present invention;

DETAILED DESCRIPTION

First Exemplary Embodiment

Detailed explanation follows regarding an exemplary embodiment of the present invention, with reference to the drawings. Note that in the following explanation, an example is used of a case in which the present invention is applied to a radiology information system that is a system that performs comprehensive management of data used in a hospital radiology department.

Figure 1:
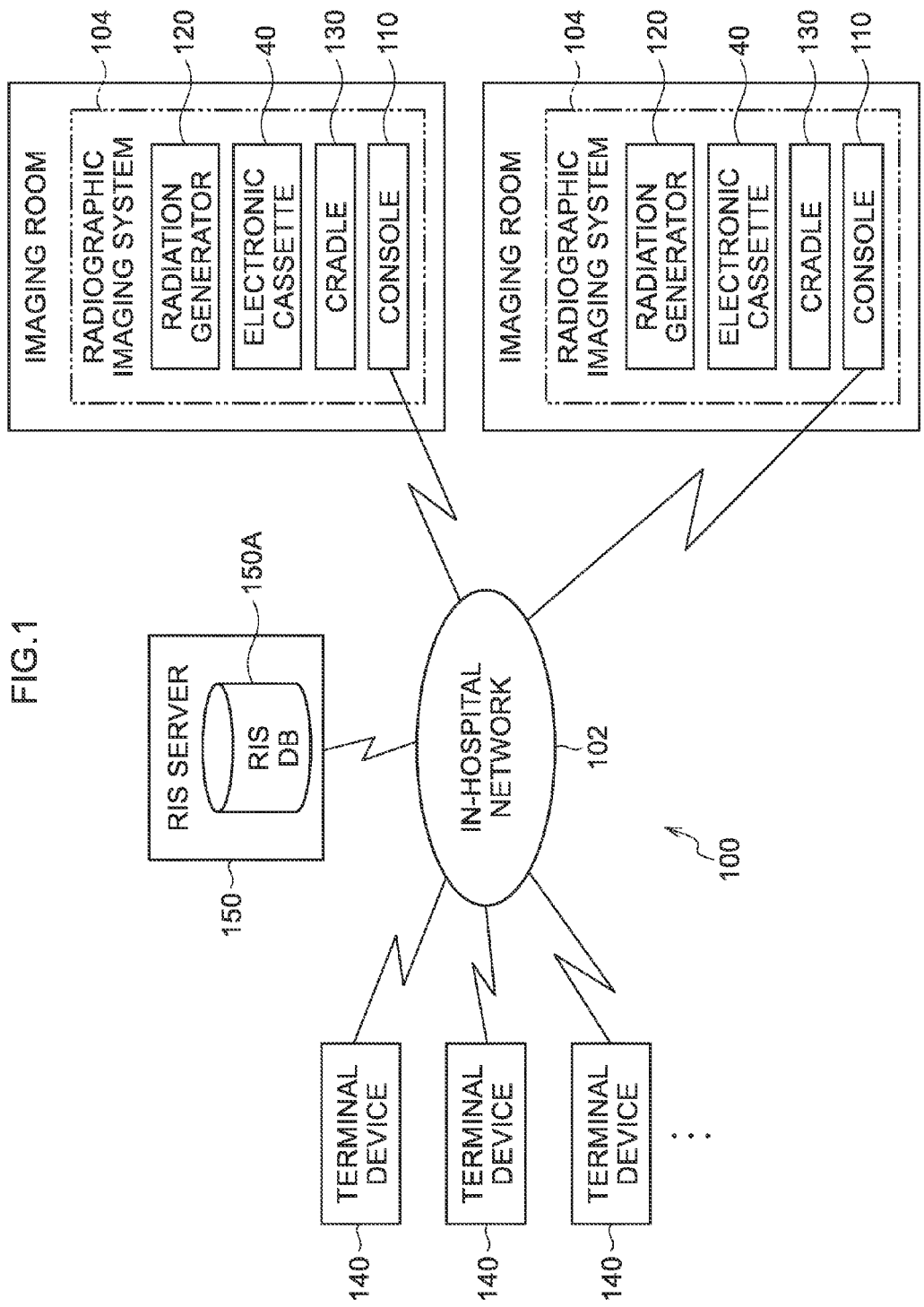
FIG. 1 is a block diagram illustrating a configuration of a radiology information system according to an exemplary embodiment of the present invention.

FIG. 1 illustrates a configuration of a radiology information system (referred to below as "RIS") 100 according to an exemplary embodiment of the present invention.

The RIS 100 is a system for managing information such as medical appointments and diagnostic records in a radiology department and configures part of a hospital information system (referred to below as "HIS").

The RIS 100 includes plural imaging request terminal devices 140 (referred to below as "terminal devices"), an RIS server 150, and radiographic imaging systems (referred to below as "imaging systems") 104. The imaging systems are installed in individual radiographic imaging rooms (or operating rooms) in a hospital. The RIS 100 is configured by the terminal devices 140, the RIS server 150. The imaging systems 104 are respectively connected to an in-hospital network 102 configured by for example a wired or wireless local area network (LAN). The RIS 100 configures part of the HIS disposed in the same hospital, and an HIS server that manages the HIS overall is also connected to the in-hospital network 102.

The terminal devices 140 are for doctors or radiographers to input and browse diagnostic information and facility reservations, and to make radiographic imaging requests and imaging reservations. Each of the terminal devices 140 includes a personal computer with a display device, and the terminal devices 140 are connected so as to be capable of communicating with each other through the RIS server 150 and the in-hospital network 102.

The RIS server 150 receives imaging requests from each of the terminal devices 140 and manages radiographic imaging schedules in the imaging systems 104. The RIS server 150 is configured including a database 150A.

The database 150A is configured including: data relating to patients (imaging subjects), such as patient attribute information (for example name, sex, date of birth, age, blood type, body weight, patient identification (ID)), medical history, consultation history, and previously captured radiographic images; data relating to electronic cassettes 40, described later, that are used in the imaging systems 104, such as identification number (ID data), model, size, sensitivity, date of first use, and numbers of times used; and environment data representing the environment in which radiographic images are captured using the electronic cassettes 40, namely the environment in which the electronic cassettes 40 are used (for example radiographic imaging room, operating room).

A doctor or radiographer operates the imaging systems 104 to perform radiographic imaging in response to an instruction from the RIS server 150. Each of the imaging systems 104 is equipped with a radiation generator 120 that irradiates the patient (imaging subject) with an amount of radiation X such as X-rays (see also FIG. 7) from a radiation source 121 (see also FIG. 9) according to exposure conditions. Each of the imaging systems 104 is also provided with the electronic cassettes 40, each of which have a built-in radiation detector 20 (see also FIG. 7) that absorbs the radiation X that has passed through an imaging target site of the patient (imaging subject) and generates charge, and generates image data expressing a radiographic image based on the amount of generated charge. The imaging systems 104 are also provided with a cradle 130 that is built into the electronic cassette 40 and charges a battery, and a console 110 that controls the electronic cassette 40 and the radiation generator 120.

The console 110 acquires various types of data included in the database 150A from the RIS server 150, stores the data in a HDD 116, described later, (see FIG. 9), and uses the data as needed to control the electronic cassette 40 and the radiation generator 120.

Figure 2:
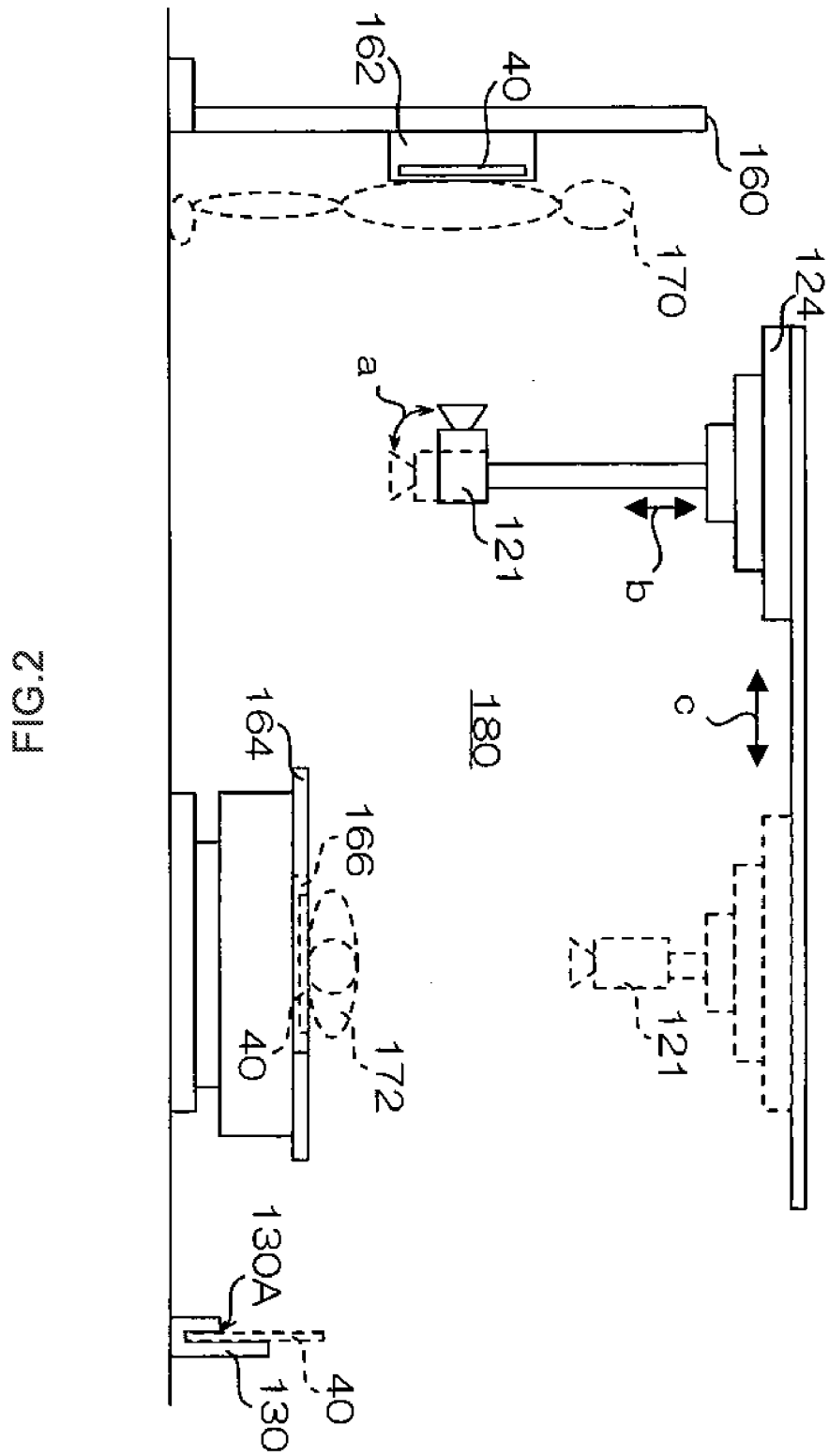
FIG. 2 is a side view illustrating an example of an installed state of each device of a radiographic imaging system according to an exemplary embodiment of the present invention in a radiographic imaging room.

FIG. 2 shows an example of an installed state of each of the devices configuring the imaging system 104 of an exemplary embodiment of the present invention in a radiographic imaging room 180.

As shown in FIG. 2, an upright stand 160 employed when performing radiographic imaging in a standing position, and a prone table 164 employed when performing radiographic imaging in a prone position, are installed in the radiographic imaging room 180. The space in front of the upright stand 160 serves as a patient (imaging subject) imaging position 170 when performing radiographic imaging in a standing position. The space above the prone table 164 serves as a patient (imaging subject) imaging position 172 when performing radiographic imaging in a prone position.

A holder 162 that holds the electronic cassette 40 is provided to the upright stand 160. The electronic cassette 40 is held by the holder 162 when capturing a radiographic image in the standing position. Similarly, a holder 166 that holds the electronic cassette 40 is provided to the prone table 164. The electronic cassette 40 is held by the holder 166 when capturing a radiographic image in the prone position.

Further, a supporting and moving mechanism 124 is disposed in the radiographic imaging room 180. The supporting and moving mechanism 124 supports the radiation source 121 in such a way that the radiation source 121 is rotatable about a horizontal axis (the direction of arrow a in FIG. 2), is movable in a vertical direction (the direction of arrow b in FIG. 2), and is movable in a horizontal direction (the direction of arrow c in FIG. 2). It is accordingly possible to employ the single radiation source 121 to perform radiographic imaging in a standing position and in a prone position.

The cradle 130 includes a housing portion 130A capable of housing the electronic cassette 40. When not in use, the electronic cassette 40 is housed in the housing portion 130A of the cradle 130, and the built-in battery of the electronic cassette 40 is charged with the electronic cassette 40 in a housed state in the housing portion 130A of the cradle 130.

In the imaging system 104, various types of data are transmitted and received by wireless communication between the radiation generator 120 and the console 110 and between the electronic cassette 40 and the console 110.

The electronic cassette 40 is not limited to being used only in a state held by the holder 162 of the upright stand 160 or the holder 166 of the prone table 164. Due to its portability the electronic cassette 40 may also be employed in a state not held by a holder, for example when imaging arm or leg regions.

Figure 3:
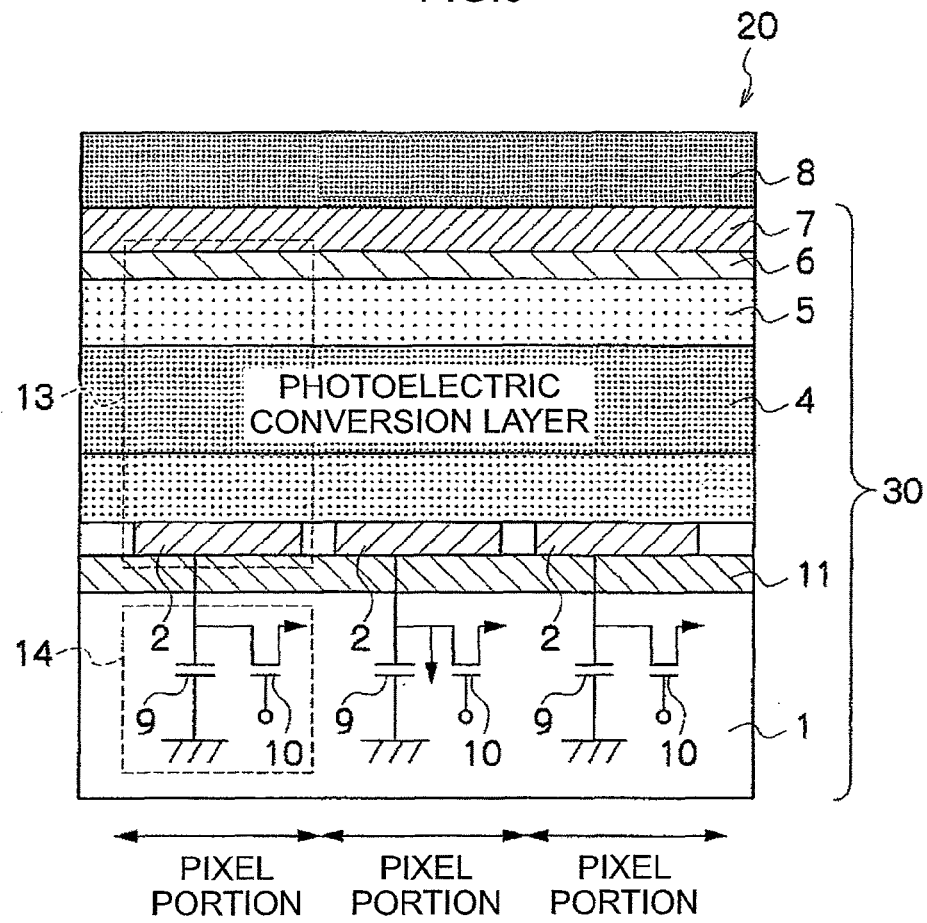
FIG. 3 is a cross-section illustrating a schematic configuration of a radiation detector according to an exemplary embodiment of the present invention.

Explanation follows regarding the configuration of the radiation detector 20 that is built into the electronic cassette 40. FIG. 3 is a cross-section schematically illustrating the configuration of a portion including three pixels of the radiation detector 20 of an exemplary embodiment of the present invention.

As shown in FIG. 3, the radiation detector 20 is configured by forming a TFT substrate 30 by forming signal output portions 14, sensor portions 13 and a transparent insulating film 7 in sequence on a substrate 1, and adhering a scintillator 8 to the TFT substrate 30 using for example an adhesive resin with low light absorbance characteristics. A pixel is configured by each of the signal output portions 14 and each of the sensor portions 13.

The scintillator 8 is formed on the sensor portions 13 with the transparent insulating film 7 interposed therebetween. The scintillator 8 includes a phosphor that converts incident radiation into light and emits the light. Namely, the scintillator 8 absorbs radiation that has passed through the patient (imaging subject) and emits light.

The wavelength region of the light emitted by the scintillator 8 is preferably in the visible light range (wavelengths of 360 nm to 830 nm). The wavelength region of the light emitted by the scintillator 8 more preferably includes the green wavelength region in order to enable monochrome imaging by the radiation detector 20.

A phosphor including cesium iodide (CsI) is preferably employed as the phosphor in the scintillator 8 in a case in which imaging employs X-rays for the radiation. CsI(Tl) (thallium-doped cesium iodide) with a light emission spectrum of 420 nm to 700 nm when X-rays are applied is particularly preferably employed. The emission peak wavelength in the visible light range of CsI(Tl) is 565 nm.

The sensor portions 13 are each configured including an upper electrode 6, a lower electrode 2, and a photoelectric conversion layer 4 that is provided between the upper electrode 6 and the lower electrode 2. The photoelectric conversion layer 4 is configured by an organic photoelectric conversion material that absorbs the light emitted by the scintillator 8 and generates charge.

The upper electrode 6 is preferably configured from a conducting material that is transparent at least with respect to the light emission wavelength of the scintillator 8 since it is necessary to allow the light produced by the scintillator 8 to be incident to the photoelectric conversion layer 4. Specifically, a transparent conducting oxide (TCO) is preferably employed that has high transmittance with respect to visible light and has a small resistance value. A metal thin film of Au or the like can also be used as the upper electrode 6, however TCO is more preferable since the resistance value increases readily when trying to obtain a transmittance of 90% or more. For example, ITO, IZO, AZO, FTO, $SnO_2$, $TiO_2$, and $ZnO_2$ can be preferably used, with ITO being the most preferred from the perspectives of ease of processing, low resistance, and transparency. The upper electrode 6 may be configured from a single sheet common to all the pixels or may be divided per pixel.

The photoelectric conversion layer 4 includes an organic photoelectric conversion material, absorbs the light emitted from the scintillator 8, and generates charge corresponding to the amount of light absorbed. The photoelectric conversion layer 4 including the organic photoelectric conversion material has a sharp absorption spectrum in the visible range, and virtually no electromagnetic waves are absorbed by the photoelectric conversion layer 4 other than the light emitted by the scintillator 8. Noise generated as a result of radiation such as X-rays being absorbed by the photoelectric conversion layer 4 can accordingly be effectively suppressed.

The absorption peak wavelength of the organic photoelectric conversion material configuring the photoelectric conversion layer 4 is preferably as close as possible to the emission peak wavelength of the scintillator 8 in order for the organic photoelectric conversion material to most efficiently absorb the light emitted by the scintillator 8. Ideally, the absorption peak wavelength of the organic photoelectric conversion material matches the emission peak wavelength of the scintillator 8. However as long as the difference between the two is small, the organic photoelectric conversion material can adequately absorb the light emitted from the scintillator 8. Specifically, the difference between the absorption peak wavelength of the organic photoelectric conversion material and the emission peak wavelength of the scintillator 8 with respect to radiation is preferably 10 nm or below. The difference is even more preferably 5 nm or below.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material for the scintillator 8, it is possible to make the difference between the peak wavelengths 5 nm or below, and the amount of charge generated in the photoelectric conversion layer 4 can be substantially maximized.

Figure 4:
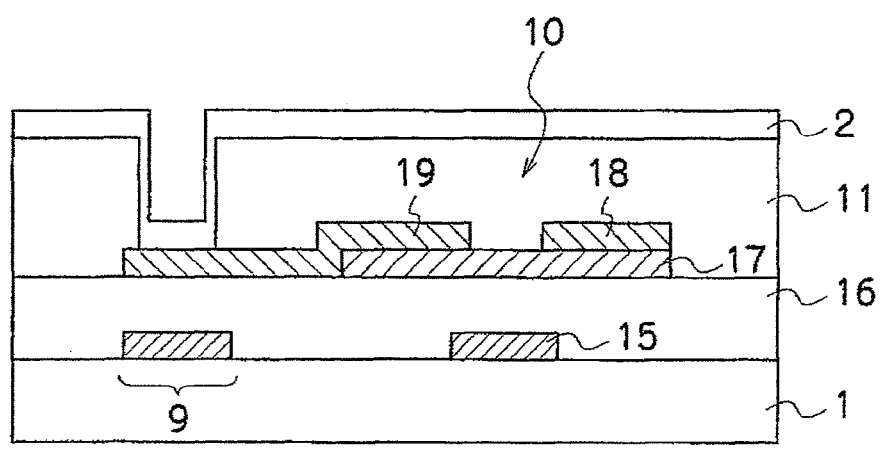
FIG. 4 is a cross-section schematically illustrating a configuration of a signal output portion of a radiation detector according to an exemplary embodiment of the present invention.

The signal output portions 14 are formed on the surface of the substrate 1 below the lower electrodes 2. FIG. 4 schematically illustrates the configuration of one of the signal output portions 14.

As shown in FIG. 4, each of the signal output portions 14 include a capacitor 9 and a field-effect thin film transistor (TFT: also referred to below simply as a "thin film transistor") 10. The capacitor 9 accumulates charge that has moved to the lower electrode 2. The thin film transistor 10 reads out the charge accumulated in the capacitor 9 into signal lines 36, described later (see FIG. 5). The capacitor 9 and the thin film transistor 10 are disposed so as to overlap with the lower electrode 2 in plan view. Namely, the signal output portion 14 and the sensor portion 13 overlap in the thickness direction in each of the pixels. In order to reduce the surface area of the radiation detector 20 (pixels), it is desirable for the region in which the capacitor 9 and the thin film transistor 10 are formed to be completely covered by the lower electrode 2.

The capacitor 9 is electrically connected to the corresponding lower electrode 2 through a wire of a conductive material that is formed penetrating an insulating film 11 disposed between the substrate 1 and the lower electrode 2. Charge collected in the lower electrode 2 can accordingly be moved to the capacitor 9.

A gate electrode 15, a gate insulating film 16, and an active layer (channel layer) 17 are stacked in the thin film transistor 10. A source electrode 18 and a drain electrode 19 are formed at a specific separation from each other on the active layer 17.

The active layer 17 may, for example, be formed by a material such as amorphous silicon, an amorphous oxide, an organic semiconductor material or carbon nanotubes. Note that the material configuring the active layer 17 is not limited to the above.

As examples of amorphous oxides that may be used to configure the active layer 17, oxides including at least one of In, Ga, and Zn (for example In—O amorphous oxides) are preferable, oxides including at least two of In, Ga, and Zn (for example In—Zn—O amorphous oxides, In—Ga—O amorphous oxides, or Ga—Zn—O amorphous oxides) are more preferable, and oxides including In, Ga, and Zn are particularly preferable. As an In—Ga—Zn—O amorphous oxide, an amorphous oxide whose composition in a crystalline state is expressed by $InGaO_3(ZnO)_m$ (where m is a natural number less than 6) is preferable, with $InGaZnO_4$ being more preferable.

Examples of organic semiconductor materials capable of configuring the active layer 17 include phthalocyanine compounds, pentacene, and vanadyl phthalocyanine, however there is no limitation thereto. Configurations of phthalocyanine compounds are described in detail in JP-A No. 2009-212389, so descriptions thereof will be omitted here.

By forming the active layer 17 of the thin film transistor 10 from an amorphous oxide, an organic semiconductor material, or carbon nanotubes, the active layer 17 does not absorb radiation such as X-rays, or this is restricted to an extremely minute amount if radiation is absorbed, so the generation of noise in the signal output portion 14 can be effectively suppressed.

Further, in a case in which the active layer 17 is formed with carbon nanotubes, the switching speed of the thin film transistor 10 can be increased, and the thin film transistor 10 can be formed having a low degree of absorption of light in the visible light range. In a case in which the active layer 17 is formed with carbon nanotubes, the performance of the thin film transistor 10 drops significantly if even a tiny amount of metal impurity is incorporated into the active layer 17, so it is necessary to separate, extract, and form extremely high-purity carbon nanotubes using centrifugal separation or the like.

Here, the amorphous oxide, organic semiconductor material, or carbon nanotubes configuring the active layer 17 of the thin film transistor 10 and the organic photoelectric conversion material configuring the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a flexible substrate, such as plastic, with aramid or bionanofibers can also be used. Specific flexible substrates that can be used include polyesters, such as polyethylene terephthalate, polybutylene phthalate and polyethylene naphthalate, polystyrene, polycarbonate, polyethersulphone, polyarylate, polyimide, polycyclic olefin, norbornene resin, and poly(chloro-trifluoro-ethylene). Employing a flexible substrate made of plastic can achieve a reduction in weight, which is advantageous from the perspective of for example portability.

Further, for example an insulating layer for ensuring insulation, a gas barrier layer for preventing the transmission of moisture and/or oxygen, and an undercoat layer for improving flatness or adhesion to the electrodes, may also be disposed on the substrate 1.

High-temperature processes of 200 degrees or higher can be applied to aramids, so a transparent electrode material can be cured at a high temperature and given a low resistance, and aramids are also compatible with automatic packaging of driver ICs including solder reflow processes. Aramids also have a thermal expansion coefficient that is close to that of indium tin oxide (ITO) or a glass substrate, so they have little warping after manufacture and do not break easily. Further, aramids can also form a thinner substrate compared to a glass substrate or the like. An ultrathin glass substrate and an aramid may also be stacked to form a substrate.

Further, bionanofibers are composites of cellulose microfibril bundles (bacterial cellulose) produced by a bacterium (Acetobacter xylinum) and a transparent resin. Cellulose microfibril bundles have a width of 50 nm, which is a size that is 1/10 visible wavelengths, and have high strength, high elasticity, and low thermal expansion. By impregnating and hardening a transparent resin such as an acrylic resin or an epoxy resin in bacterial cellulose, bionanofibers can be obtained that exhibit a light transmittance of about 90% at a wavelength of 500 nm while including fibers at 60 to 70%. Bionanofibers have a low thermal expansion coefficient (3 to 7 ppm) comparable to silicon crystal, a strength comparable to steel (460 MPa), high elasticity (30 GPa), and are flexible, thereby enabling the substrate 1 to be formed thinner compared for example to a glass substrate.

Figure 5:
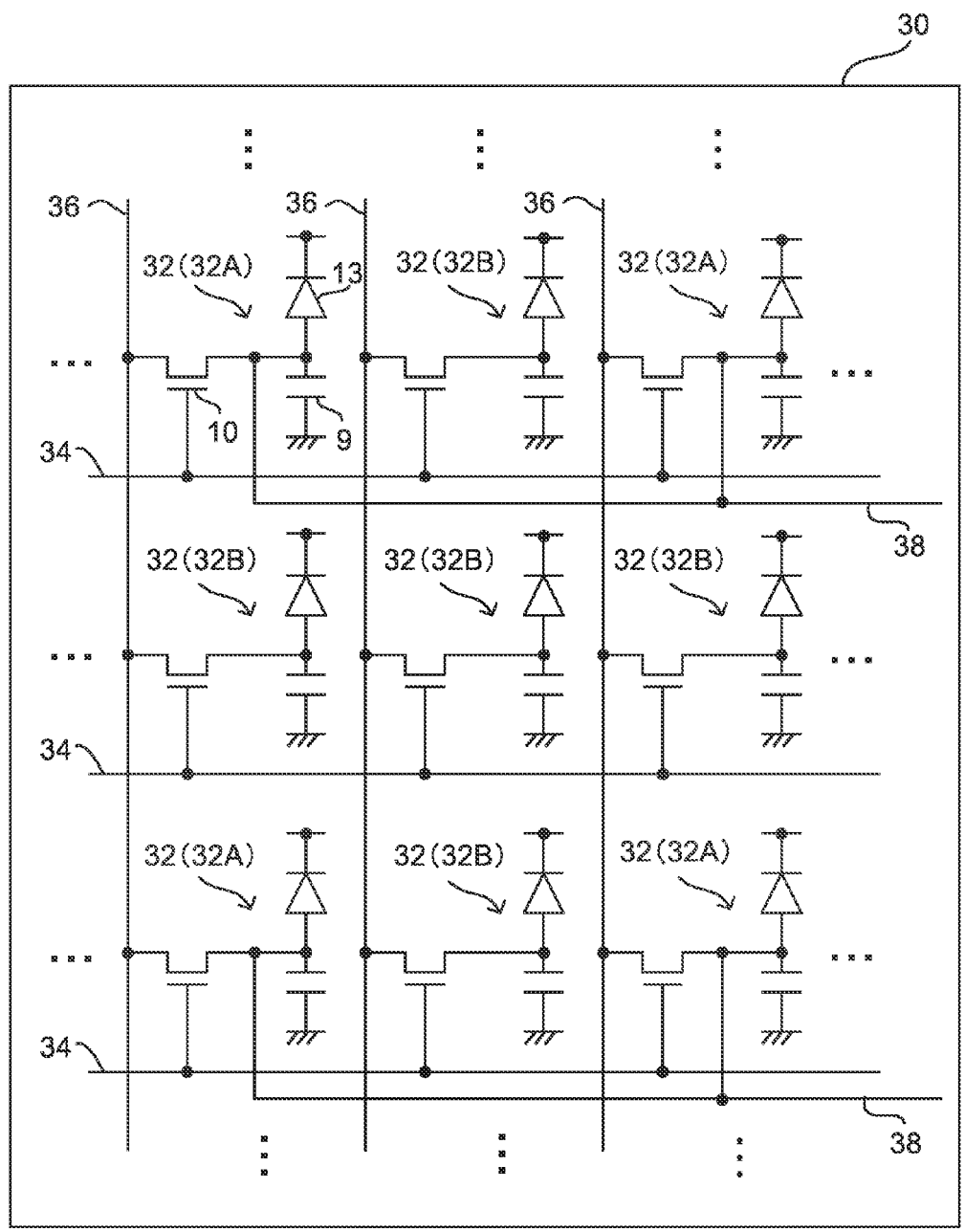
FIG. 5 is a diagram illustrating a configuration of a TFT substrate according to an exemplary embodiment of the present invention.

FIG. 5 is a plan view illustrating a configuration of the TFT substrate 30 configuring the radiation detector 20. As shown in FIG. 5, plural pixels 32 each configured including the sensor portion 13, the capacitor 9, and the thin film transistor 10 are disposed on the TFT substrate 30 in a two-dimensional pattern in one direction (the row direction in FIG. 5) and an direction intersecting the one direction (the column direction in FIG. 5).

The TFT substrate 30 is disposed with plural gate lines 34 that extend in the one direction (the row direction) and that switch each of the thin film transistors 10 ON and OFF, and the plural signal lines 36 that extend in the intersecting direction (the column direction) and that read the charges through the thin film transistors 10 that are in an ON state. Each of the sensor portions 13 is supplied with a bias voltage through a bias line.

The TFT substrate 30 is formed in flat plate shape, and in a quadrilateral shape having four sides on its outer edges in plan view. More specifically, the TFT substrate 30 is formed in a rectangular shape.

The TFT substrate 30 includes pixels 32 that are employed to detect the presence or absence of radiation irradiation, and pixels 32 that capture a radiographic image. In the following explanation, the pixels 32 that detect radiation will be referred to as radiation detection pixels 32A, and the remaining pixels 32 will be referred to as radiographic imaging pixels 32B. In the electronic cassette 40 of the present exemplary embodiment, the start of radiation irradiation is detected using the radiation detection pixels 32A.

Connection portions between the capacitors 9 configuring the radiation detection pixels 32A and the thin film transistor 10 are connected to direct read lines 38. Pixel data for radiation detection obtained from the radiation detection pixels 32A is transmitted to a second signal processor 55, described later, through the direct read lines 38, and subjected to processing to detect radiation irradiation start by the second signal processor 55.

Figure 6:
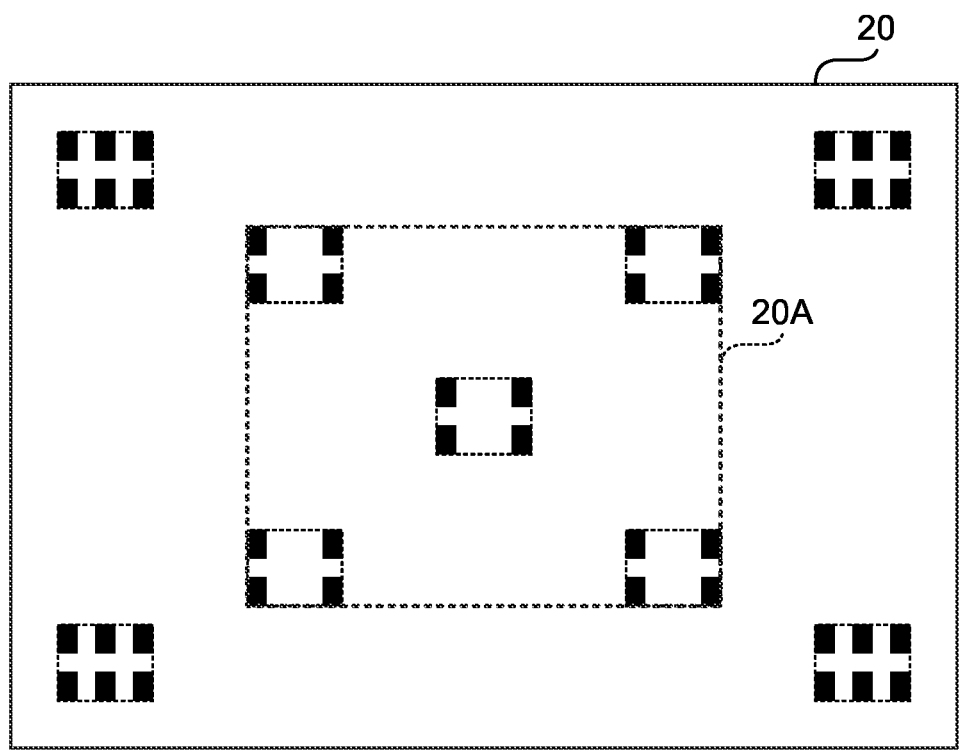
FIG. 6 is a plan view illustrating the disposal of radiation detection pixels according to an exemplary embodiment of the present invention.

Note that the radiation detection pixels 32A may be disposed with uniform distribution on the TFT substrate 30. Moreover, as shown in the example in FIG. 6, the radiation detection pixels 32A may be disposed at a comparatively low density in a partial region (a rectangular region centered on a central portion of an imaging region of the radiation detector 20 in the present exemplary embodiment) 20A that includes the central portion of the imaging region, and disposed at a comparatively high density at regions peripheral thereto. Disposing the radiation detection pixels 32A in this way makes it possible to detect radiation irradiation start more accurately since the surface area of the radiation detection pixels 32A that are disposed at the exposed portion where the radiation detection pixels 32A do not overlap with the imaging target site during imaging can be increased.

In the TFT substrate 30, it is not possible to obtain radiographic image pixel data for the positions where the radiation detection pixels 32A are disposed within the imaging region. Accordingly, in the TFT substrate 30 the radiation detection pixels 32A are disposed so as to be dispersed within the imaging region, and missing pixel correction processing is executed by the console 110 to interpolate radiographic image pixel data for the positions where the radiation detection pixels 32A are disposed, by employing pixel data obtained from the radiographic imaging pixels 32B positioned peripherally to the radiation detection pixels 32A.

Figure 7:
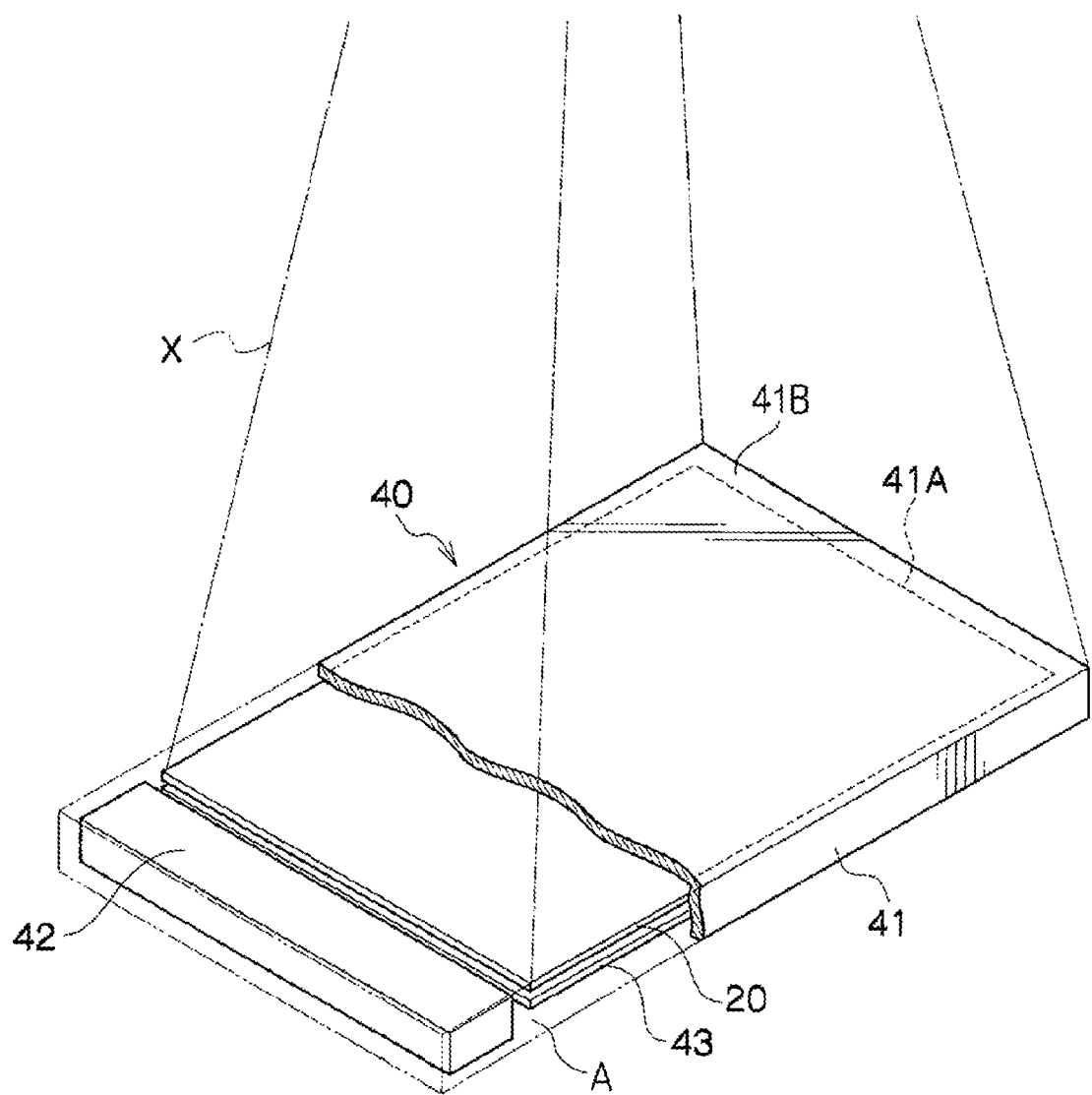
FIG. 7 is a perspective view illustrating a configuration of an electronic cassette according to an exemplary embodiment of the present invention.

Explanation next follows regarding the configuration of the electronic cassette 40 according to the present exemplary embodiment. FIG. 7 is a perspective view illustrating a configuration of the electronic cassette 40 of an exemplary embodiment of the present invention.

As shown in FIG. 7, the electronic cassette 40 is equipped with a housing 41 that is formed from a material that allows radiation to pass through, and the electronic cassette 40 is configured with a waterproof and airtight structure. There is a concern that blood or other contaminants may adhere to the electronic cassette 40 when the electronic cassette 40 is used for example in an operating room. Therefore, giving the electronic cassette 40 a waterproof and airtight structure enables a single electronic cassette 40 to be used repeatedly by disinfecting the electronic cassette 40 as required.

A space A that accommodates various components is formed inside the housing 41. The radiation detector 20 that detects the radiation X that has passed through the patient (imaging subject), and a lead plate 43 that absorbs backscattered rays of the radiation X, are disposed inside the space A in this order from an irradiated face side of the housing 41 that is irradiated with the radiation X.

A region corresponding to the placement position of the radiation detector 20 configures an imaging region 41A that is capable of detecting the radiation. The face of the housing 41 with the imaging region 41A is configured as a top plate 41B of the electronic cassette 40. In the electronic cassette 40 of the present exemplary embodiment, the radiation detector 20 is disposed so that the TFT substrate 30 is on the top plate 41B side, and in the housing 41 the TFT substrate 30 is adhered to the inside face of the top plate 41B (the face of the top plate 41B at the opposite side of the face to which radiation is incident).

As shown in FIG. 7, a case 42 that accommodates a cassette controller 58, described later, and a power source unit 70 (see FIG. 9 for both), is placed at one end side of the interior of the housing 41 at a position that does not overlap with the radiation detector 20 (outside the range of the imaging region 41A).

The housing 41 is for example configured from carbon fiber, aluminum, magnesium, bionanofibers (cellulose microfibrils), or a composite material, in order to achieve a reduction in weight for the electronic cassette 40 overall.

As a composite material, for example, a material including a reinforcement fiber resin is used, with for example carbon or cellulose incorporated in the reinforcement fiber resin. Specific examples of composite materials that may be used include carbon fiber reinforced plastic (CFRP), a composite material with a structure where a foam material is sandwiched by CFRP, or a composite material in which the surface of a foam material is coated with CFRP. In the present exemplary embodiment, a composite material with a structure in which a foam material is sandwiched by CFRP is used. The strength (rigidity) of the housing 41 can accordingly be raised compared to a case in which the housing 41 is configured by a carbon element.

Figure 8:
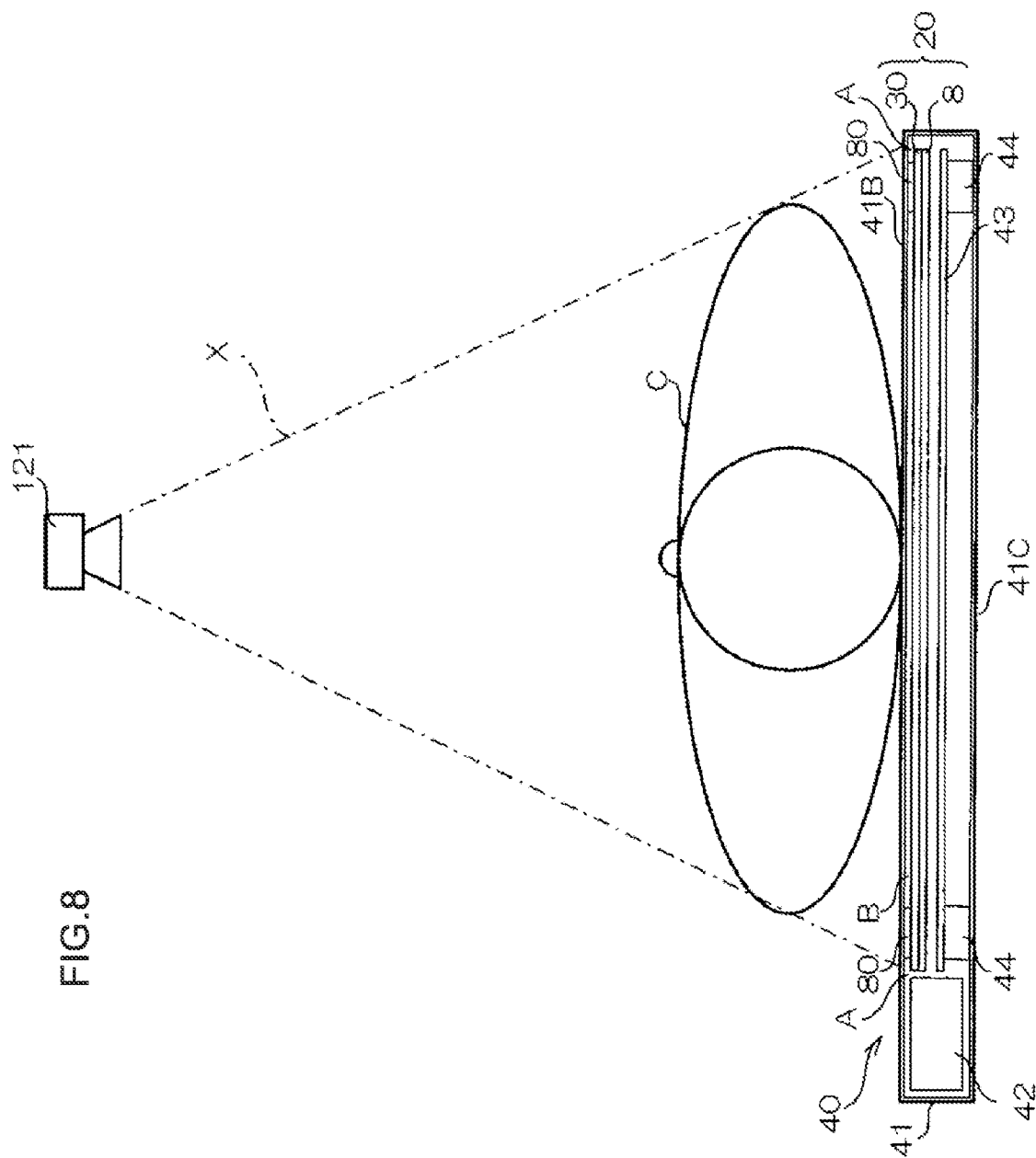
FIG. 8 is a cross-section illustrating a configuration of an electronic cassette according to an exemplary embodiment of the present invention.

FIG. 8 is a cross-section illustrating a configuration of the electronic cassette 40. As shown in FIG. 8, support members 44 are disposed inside the housing 41 on the inner face of a back face portion 41C that faces the top plate 41B. The radiation detector 20 and the lead plate 43 are arrayed in this order along the radiation X application direction between the support members 44 and the top plate 41B. The support members 44 support the lead plate 43 and, from the perspective of weight reduction and the perspective of absorbing dimensional deviation, are configured by for example a foam material.

As shown in FIG. 8, adhesive members 80 are provided at the inner face of the top plate 41B to detachably adhere the TFT substrate 30 of the radiation detector 20. Double-sided tape, for example, can be employed for the adhesive members 80. In this case, the double-sided tape is formed in such a way that the adhesive force of one adhesive face is stronger than that of the other adhesive face.

Specifically, the face with the weaker adhesive force (weak adhesive face) is set to have a 180-degree peel strength of 1.0 N/cm or lower. The face with the stronger adhesive force (strong adhesive face) contacts the top plate 41B, and the weaker adhesive face contacts the TFT substrate 30. The thickness of the electronic cassette 40 can accordingly be made thinner than in a case in which the radiation detector 20 is fixed to the top plate 41B by, for example, fixing members such as screws. Moreover, even if the top plate 41B deforms under impact or load, the radiation detector 20 follows the deformation of the top plate 41B that has high rigidity, so only deformation of large radius of curvature (a gentle curve) arises, reducing the likelihood of the radiation detector 20 sustaining damage due to localized deformation of low radius of curvature. Moreover, the radiation detector 20 contributes to raising the rigidity of the top plate 41B.

Thus in the electronic cassette 40 according to the present exemplary embodiment, since the radiation detector 20 is adhered at the inside of the top plate 41B of the housing 41, the housing 41 is separable into two between the top plate 41B side and the back face portion 41C side. The housing 41 is placed in a state divided into the two parts of the top plate 41B side and the back face portion 41C side in order to adhere the radiation detector 20 to the top plate 41B or detach the radiation detector 20 from the top plate 41B.

In the present exemplary embodiment, adhering the radiation detector 20 to the top plate 41B does not have to be performed for example in a clean room. This is due to the fact that even if foreign objects such as metal fragments that absorb radiation where to be incorporated between the radiation detector 20 and the top plate 41B, such foreign objects can be removed by detaching the radiation detector 20 from the top plate 41B.

Figure 9:
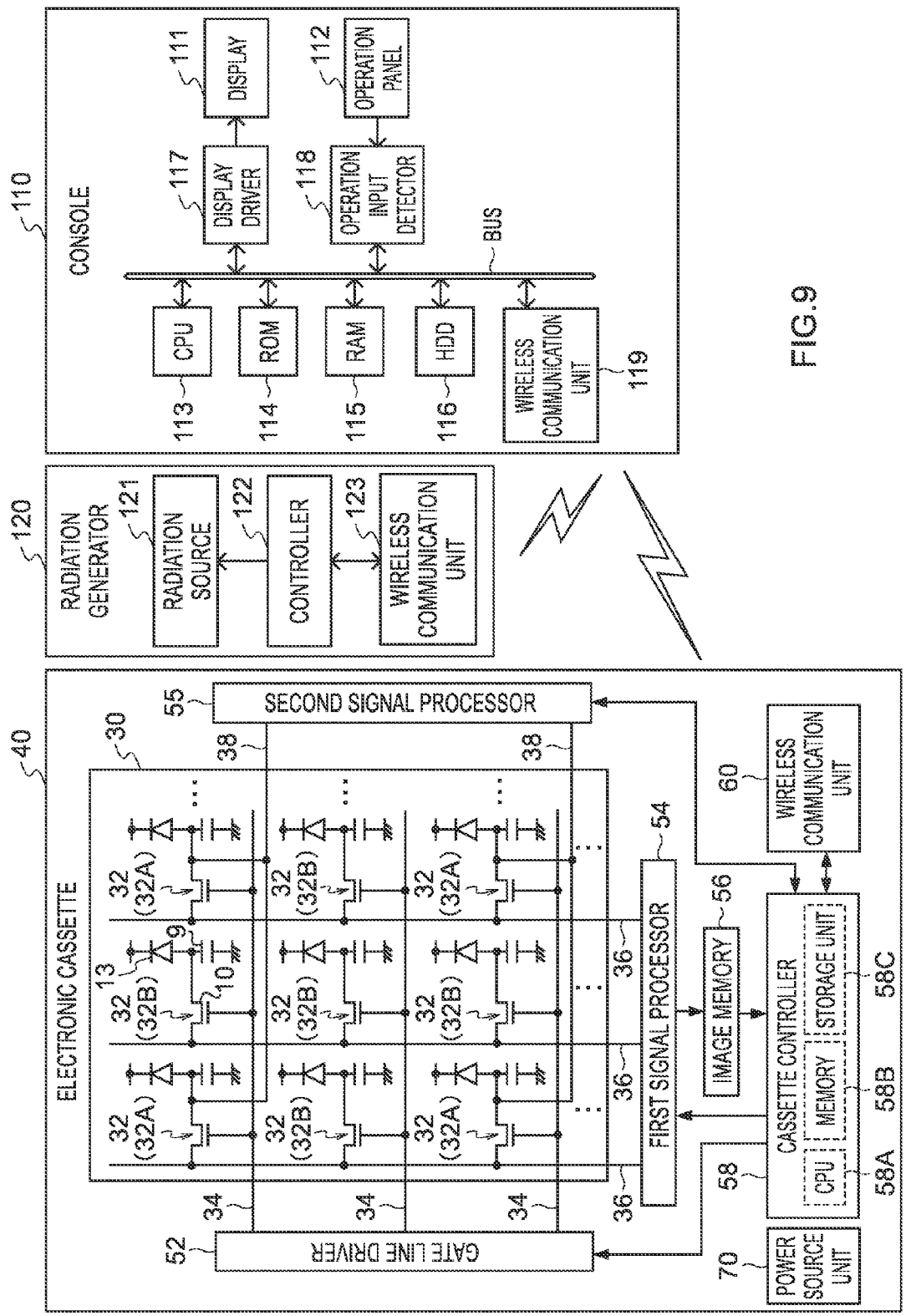
FIG. 9 is a block diagram illustrating a configuration of relevant portions of an electrical system of a radiographic imaging system according to an exemplary embodiment of the present invention.

FIG. 9 is a drawing illustrating a configuration of relevant portions of an electrical system of the imaging system 104 of the present exemplary embodiment. As shown in FIG. 9, in the TFT substrate 30 configuring the radiation detector 20 built into the electronic cassette 40, a gate line driver 52 is disposed on one side of two adjacent sides, and a first signal processor 54 is disposed on the other side. The individual gate lines 34 of the TFT substrate 30 configuring the radiation detector 20 are connected to the gate line driver 52, and the individual signal lines 36 of the TFT substrate 30 are connected to the first signal processor 54.

An image memory 56, the cassette controller 58, a wireless communication unit 60, and the power source unit 70 are provided inside the housing 41.

Each of the thin film transistors 10 of the TFT substrate 30 are switched ON in sequence in row units by signals supplied through the gate lines 34 from the gate line driver 52, and the charges that have been read out by the thin film transistors 10 being switched to an ON state are transmitted through the signal lines 36 as electric signals and input to the first signal processor 54. The charges are thereby read out in sequence by row unit, and a two-dimensional radiographic image is acquired.

The first signal processor 54 is configured including charge amplifiers, sample-and-hold circuits, a multiplexer and an analogue-to-digital (A/D) converter. The charge amplifiers generate electric signals with a voltage level corresponding to the amount of charge read out from the sensor portions 13 through each of the signal lines 36. The signal levels of the electric signals generated by the charge amplifiers are held by the sample-and-hold circuits. Output terminals of the sample-and-hold circuits are connected to the common multiplexer. The multiplexer converts the signal levels held by the sample-and-hold circuits into serial data and supplies this serial data to the A/D converter. The A/D converter converts the analogue electric signals supplied from the multiplexer into image data as digital signals.

The image memory 56 is connected to the first signal processor 54. The image data output from the A/D converter of the first signal processor 54 are sequentially stored in the image memory 56. The image memory 56 has a storage capacity that is capable of storing a predetermined number of frames' worth of image data. The image data obtained by the imaging are sequentially stored in the image memory 56 each time radiographic imaging is performed. The image memory 56 is also connected to the cassette controller 58.

The cassette controller 58 performs overall control of the operation of the entire electronic cassette 40. The cassette controller 58 is configured including a microcomputer, and is equipped with a central processing unit (CPU) 58A, a memory 58B including read-only memory (ROM) and random access memory (RAM), and a nonvolatile storage unit 58C configured for example by flash memory. The wireless communication unit 60 is connected to the cassette controller 58.

The wireless communication unit 60 conforms to a wireless local area network (LAN) standard such as typified by the Institute of Electrical and Electronics Engineers (IEEE) 802.11a/b/g and controls the transmission of various types of data to and from external devices by wireless communication. Through the wireless communication unit 60, the cassette controller 58 enabled for wireless communication with external devices such as the console 110 that performs control relating to radiographic imaging and is enabled for transmitting and receiving various types of data to and from the console 110, for example.

The electronic cassette 40 is provided with the power source unit 70, with various circuits and devices (the gate line driver 52, the first signal processor 54, the second signal processor 55, the image memory 56, the wireless communication unit 60 and the microcomputer that functions as the cassette controller 58) actuated with power supplied from the power source unit 70. The power source unit 70 has an inbuilt battery (a rechargeable secondary battery) so as not to affect the portability of the electronic cassette 40, and power is supplied to the various circuits and devices from the charged battery. Note that wiring that connects the power source unit 70 to the various circuits and devices is omitted from illustration in FIG. 9.

The second signal processor 55 is placed on the opposite side of the TFT substrate 30 to the gate line driver 52 with the TFT substrate 30 in between. The direct read lines 38 connected to each of the radiation detection pixels 32A are also connected to the second signal processor 55. Pixel data for radiation detection obtained from the radiation detection pixels 32A is transmitted through the direct read lines 38 to the second signal processor 55. The second signal processor 55 performs processing to detect irradiation start based on the pixel data supplied from the radiation detection pixels 32A.

Figure 10:
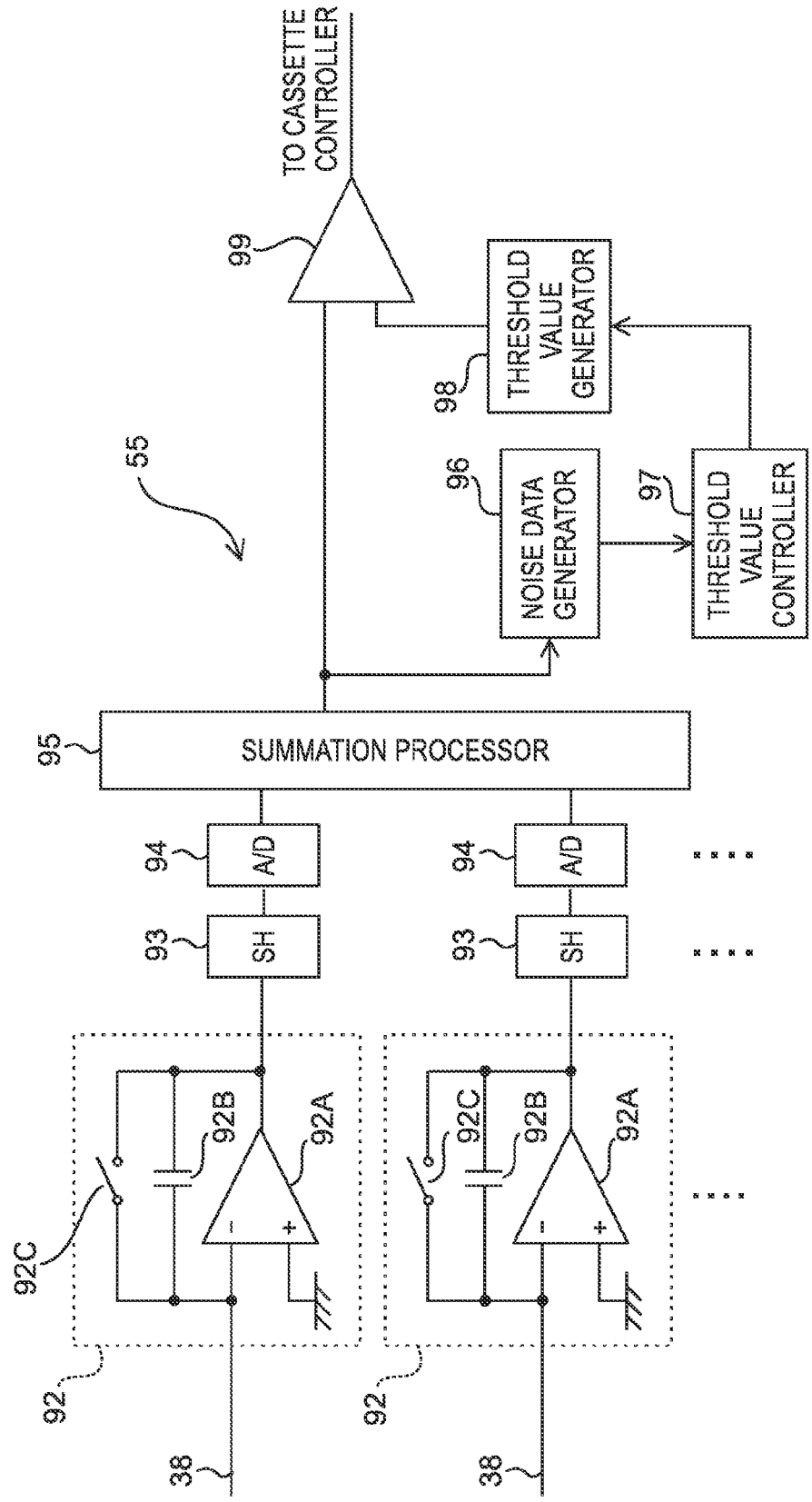
FIG. 10 is a diagram illustrating a configuration of a second signal processor according to an exemplary embodiment of the present invention.

FIG. 10 illustrates a configuration of the second signal processor 55. As shown in FIG. 10, the second signal processor 55 includes charge amplifiers 92 connected to each of the direct read lines 38. Each of the charge amplifiers 92 includes: an operational amplifier (operation amplification circuit) 92A with inverting input terminal connected to the respective direct read line 38 and non-inverting input terminal connected to a ground potential; a capacitor 92B with one terminal connected to the inverting input terminal of the operational amplifier 92A and the other terminal is connected to the output terminal of the operational amplifier 92A; and a reset switch 92C that is connected in parallel to the capacitor 92B.

The charges generated in each of the radiation detection pixels 32A are accumulated in the capacitors 92B of the charge amplifiers 92 through the direct read lines 38. The charge amplifiers 92 generate electric signals with a signal level corresponding to the charge amount supplied from the radiation detection pixels 32A and accumulated in the capacitors 92B. These electric signals are supplied to sample-and-hold circuits 93. The electric signals output from the charge amplifiers 92 are reset when the reset switches 92C are switched ON in response to a control signal supplied from the cassette controller 58.

The sample-and-hold circuits 93 hold the signal level of the electric signals supplied from the charge amplifiers 92 in response to a control signal supplied from the cassette controller 58. The held signal levels are supplied to A/D converters 94. Namely, the sample-and-hold circuits 93 perform sampling of the signal levels of the electric signals output from the charge amplifiers 92 at a specific sampling cycle in response to control signals supplied from the cassette controller 58.

The A/D converters 94 convert the signal levels of the electric signals supplied in sequence from the sample-and-hold circuits 93 into digital signals, and digital values obtained thereby are supplied to a summation processor 95.

The summation processor 95 sums together the digital signal values supplied from each of the A/D converters 94, and supplies the summed value obtained to a comparator 99 and to a noise data generator 96. Namely, the summation processor 95 generates a signal value according to the total sum of the amount of charge generated in each of the radiation detection pixels 32A for each sampling cycle. Note that a reset cycle of the charge amplifiers 92 and the sampling cycle of the sample-and-hold circuits 93 are mutually synchronized to the operation of the A/D converters 94 and the summation processor 95.

The comparator 99 compares the signal value output from the summation processor 95 against a threshold value output from a threshold value generator 98, and a high level output signal is generated when the signal value output from the summation processor 95 exceeds the threshold value. The output terminal of the comparator 99 is connected to the cassette controller 58. Radiation exposure from the radiation source 121 is determined to have started when the cassette controller 58 receives a high level signal from the comparator 99.

The threshold value generator 98 generates the threshold value used in comparison processing by the comparator 99. The threshold value output from the threshold value generator 98 is set at a value derived by a threshold value controller 97.

Figure 11:
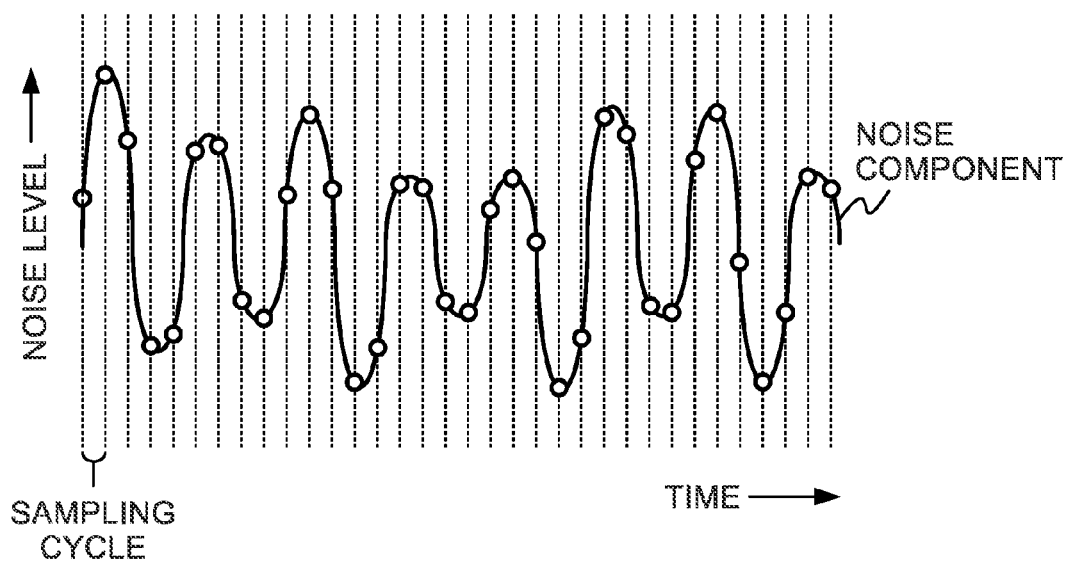
FIG. 11 is a diagram illustrating noise level sampling processing in a second signal processor according to an exemplary embodiment of the present invention.

As well as generating signal charge according to the radiation irradiation amount emitted from the radiation source 121, the radiation detection pixels 32A also generate dark charge whether or not incident radiation is present. A noise component caused by this dark charge is therefore incorporated in the direct read lines 38 connected to the radiation detection pixels 32A. Moreover, a noise component caused by external noise sources is sometimes incorporated when the electronic cassette 40 is installed in a noisy environment affected by external noise sources such as magnetic fields, electromagnetic waves and vibrations. As shown in FIG. 11, in a non-irradiation state in which radiation is not being emitted from the radiation source 121, a noise level sampling value of noise caused by dark charge and by external noise sources is output from the summation processor 95 at each sampling cycle by driving the second signal processor 55.

The noise data generator 96 is configured including a microcomputer and is equipped with a CPU, ROM and RAM. In a non-irradiation state prior to radiation being emitted from the radiation source 121, the noise data generator 96 collects, as noise level sampling values, signal values sequentially supplied from the summation processor 95 at each sampling cycle, and generates a statistical value of sampling values that serves as noise data expressing a noise state.

Figure 12:
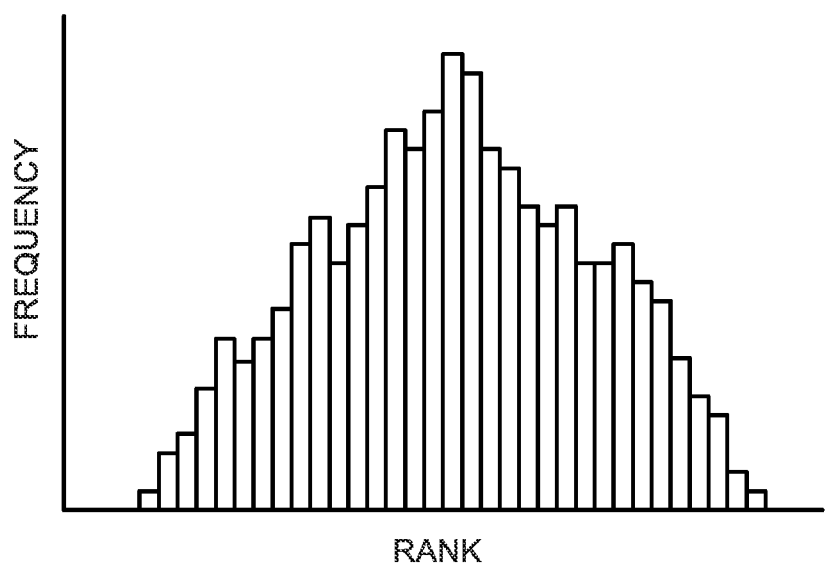
FIG. 12 is a histogram of noise level generated by a noise data generator according to an exemplary embodiment of the present invention.

The noise data generator 96 generates a histogram, such as the example shown in FIG. 12, from the signal values (noise level sampling values) sequentially supplied from the summation processor 95 in the non-irradiation state of radiation. The horizontal axis in FIG. 12 shows ranks of noise level and the vertical axis shows frequency. As well as generating such a histogram, the noise data generator 96 also generates as the noise data a statistical value such as a maximum value Amax, a minimum value Amin, an average value p, a variance $\sigma^2$, or a standard deviation $\sigma$ for the sampled values.

Note that in the present exemplary embodiment, the noise data generator 96 continues noise level sampling until radiation irradiation start is detected, and builds up the number of samplings used in the generation of the histogram and the noise data. Accompanying this, the noise data generator 96 sequentially updates the histogram and the noise data each time a new sampling value is added.

Configuration may be made such that the second signal processor 55 does not perform unlimited noise level sampling in the period until radiation irradiation start is detected, and instead performs noise level sampling within a given interval until a specific duration has elapsed from the start of noise level sampling. The noise data generator 96 then generates the histogram and the noise data based on sampling values sampled in this interval.

The noise level sampling start time and end time in the second signal processor 55 may also be set manually. For example, a sampling start button and a sampling stop button may be provided to the electronic cassette 40 for instructing a noise level sampling start time and a noise level sampling stop time to the cassette controller 58. In such cases, the cassette controller 58 supplies a control signal to the second signal processor 55 when the radiographer presses the sampling start button, and noise level sampling is started. The cassette controller 58 also supplies a control signal to the second signal processor 55 when the radiographer presses the sampling stop button, and noise level sampling is stopped. The noise data generator 96 then generates a histogram and noise data generated based on the sampling values acquired in the period between the sampling start button being pressed and the sampling stop button being pressed. Note that the noise level sampling start time and stop time may also be instructed using a remote controller.

The advantageous effect of a saving in power consumption for the electronic cassette 40 may accordingly be expected due to thus limiting the time period for noise level sampling.

The noise data generator 96 may also generate a histogram and noise data for a specific number of times of sampling n. In such cases, the noise data generator 96 may update the histogram and the noise data each time a new sampling value is supplied from the summation processor 95, or the histogram and the noise data may be updated at the point at which n new sampling values have been supplied from the summation processor 95.

The threshold value controller 97 is configured including a microcomputer and is equipped with a CPU, ROM and RAM. The threshold value controller 97 derives a threshold value at which the comparator 99 determines radiation irradiation start based on the noise data generated by the noise data generator 96. The threshold value controller 97 derives a higher threshold value the higher the variation in noise level expressed in the noise data. The threshold value controller 97 may employ a difference value between the minimum value Amin and the maximum value Amax of the sampling values as a variation indicator value to indicate the amount of noise level variation, or may employ the variance $\sigma^2$ or the standard deviation $\sigma$ therefor. The threshold value controller 97 derives a higher threshold value the higher the variation indicator value, thereby setting a lower detection sensitivity for radiation irradiation start.

In the present exemplary embodiment, the threshold value controller 97 extracts the noise level average value $\mu$ and standard deviation $\sigma$ from the noise data generated by the noise data generator 96, and derives as the threshold value $\mu+m\sigma$ (where m is a value of 1 or greater). In cases in which the distribution of the noise level follows a normal distribution, supposing that m=4 (namely that the threshold value is $\mu+4\sigma$), then 99.9937% of the signal values output in sequence from the summation processor 95 in a non-radiation irradiated state fall below the threshold value, enabling false detection of radiation irradiation start caused by noise to be greatly reduced.

The threshold value controller 97 controls the threshold value of the threshold value generator 98 so as to be a threshold value derived as described above. The noise data generator 96 updates the histogram and noise data, and then the threshold value controller 97 derives a new threshold value according to the updated histogram and noise data. Namely, the threshold value controller 97 derives a threshold value based on the most up-to-date noise data, thereby varying the threshold value appropriately according to noise generation conditions.

As shown in FIG. 9, the console 110 is configured by a server/computer, and is equipped with a display 111 that displays for example an operation menu and captured radiographic images, and an operation panel 112 that is configured including plural keys and is input with various types of information and operation instructions.

Moreover, the console 110 according to the present exemplary embodiment is equipped with: a CPU 113 that controls operation of the overall apparatus; ROM 114 that is pre-stored with for example various programs including a control program; RAM 115 that temporarily stores various data; a hard disk drive (HDD) 116 that stores and holds various data; a display driver 117 that controls the display of various information on the display 111; and an operation input detector 118 that detects an operation state of the operation panel 112. The console 110 is further equipped with a wireless communication unit 119 that employs wireless communication to transmit and receive various data such as exposure conditions, described later, between the console 110 and the radiation generator 120, as well as transmitting and receiving various data such as image data between the console 110 and the electronic cassette 40.

The CPU 113, the ROM 114, the RAM 115, the HDD 116, the display driver 117, the operation input detector 118 and the wireless communication unit 119 are connected together through a system bus BUS. The CPU 113 can accordingly access the ROM 114, the RAM 115 and the HDD 116, and the CPU 113 can also control the display of various data on the display 111 through the display driver 117, and control the transmission and reception through the wireless communication unit 119 of various data to and from the radiation generator 120 and the electronic cassette 40. The CPU 113 can also ascertain the operation state of the operation panel 112 by a user through the operation input detector 118.

Configuration is made so that the histogram and the noise data generated in the noise data generator 96 of the second signal processor 55 is transmitted to the console 110 through the wireless communication unit 119 and displayed on the display 111.

The radiation generator 120 is equipped with the radiation source 121, a wireless communication unit 123 that transmits and receives various data such as exposure conditions between the radiation generator 120 and the console 110, and a controller 122 that controls the radiation source 121 based on received exposure conditions.

The controller 122 is also configured including a microcomputer, and stores received exposure conditions. These exposure conditions received from the console 110 include data such as tube voltage, tube current, and exposure duration. The controller 122 causes the radiation X to be irradiated from the radiation source 121 based on the received exposure conditions.

Explanation next follows regarding operation of the imaging system 104 of the present exemplary embodiment.

Figure 13:
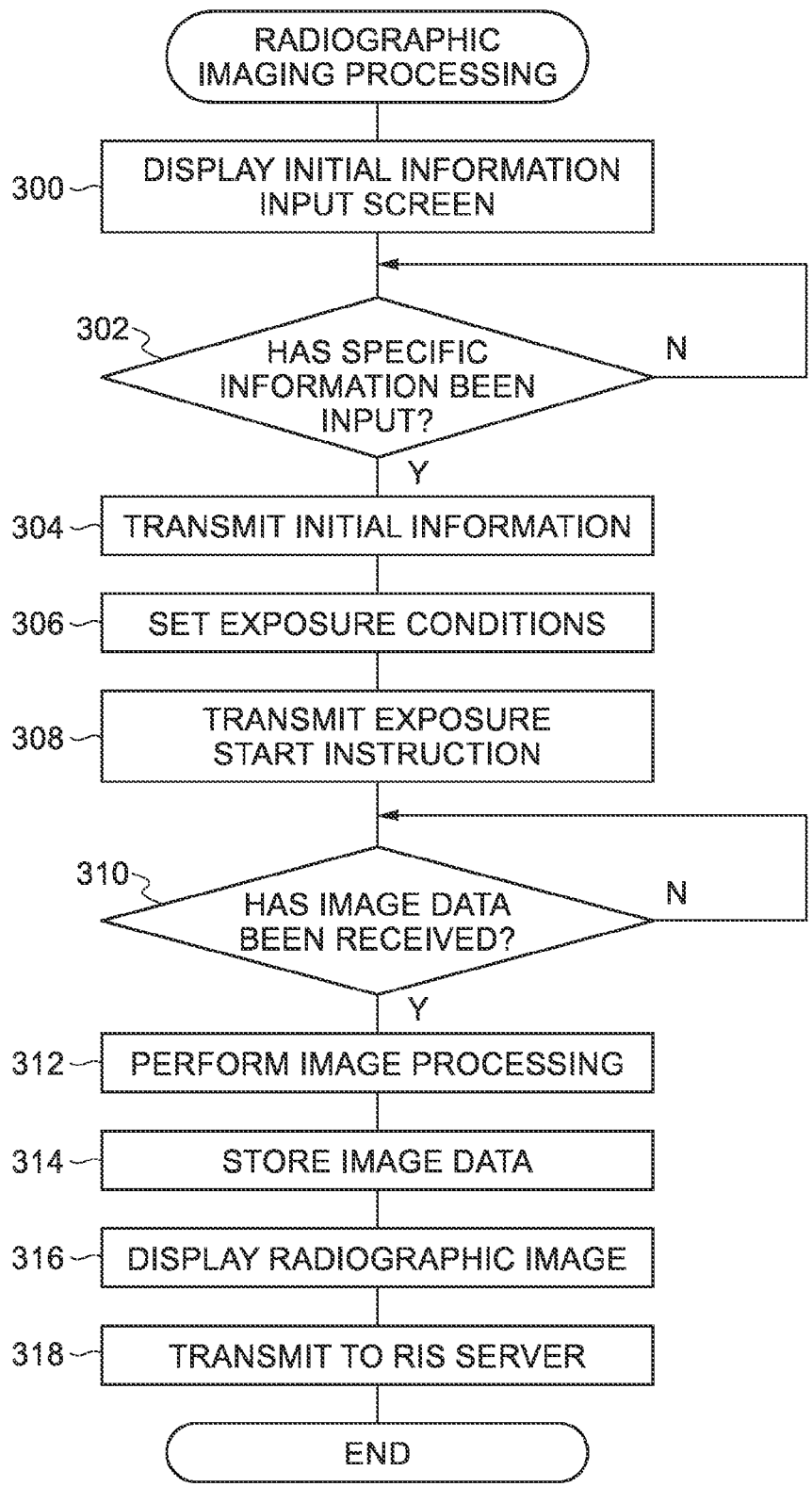
FIG. 13 is a flow chart illustrating a processing flow in a radiographic imaging processing program according to an exemplary embodiment of the present invention.

First, explanation follows regarding the operation of the console 110 when capturing a radiographic image, with reference to FIG. 13. FIG. 13 is a flow chart showing a flow of processing by a radiographic imaging processing program that is executed by the CPU 113 of the console 110 when input with an instruction to execute radiographic imaging through the operation panel 112. This program is pre-stored in a predetermined region of the ROM 114.

At step 300 in FIG. 13, the CPU 113 controls the display driver 117 so as to cause the display 111 to display a predetermined initial information input screen. At the next step 302, the CPU 113 is on standby for input of specific information.

FIG. 14 shows an example of the initial information input screen that is displayed on the display 111 by the processing of step 300. As shown in FIG. 14, in the initial information input screen according to the present exemplary embodiment, a message is displayed prompting input of the name of the patient (imaging subject) on whom radiographic imaging is to be performed, the imaging target site, the posture during imaging, and the exposure conditions of the radiation X during imaging (in the present exemplary embodiment, the tube voltage, the tube current and exposure duration during radiation X exposure). Input fields for these items of information are also displayed.

After the initial information input screen shown in FIG. 14 is displayed on the display 111, the radiographer inputs the name of the patient (imaging subject) to be imaged, the imaging target site, the posture during imaging, and the exposure conditions into the corresponding input fields through the operation panel 112.

The radiographer enters the radiographic imaging room 180 with the patient (imaging subject). When performing image capture in a standing position or prone position, the radiographer positions the patient (imaging subject) at a specific imaging position (performs positioning) after the electronic cassette 40 has been held by holder 162 of the upright stand 160 or the holder 166 of the prone table 164 as appropriate and the radiation source 121 has been positioned correspondingly. However in order to perform radiographic imaging with the electronic cassette 40 not held by a holder, such as when the imaging target site is a region of an arm or leg, the radiographer positions the patient (imaging subject) in a specific imaging position (performs positioning). However, when capturing a radiographic image of an imaging target site such as an arm or a leg without the electronic cassette 40 being held in the holders, the radiographer positions (performs positioning of) the patient (imaging subject), the electronic cassette 40 and the radiation source 121 in a state that allows imaging of the imaging target site.

The radiographer then exits the radiographic imaging room 180, and uses the operation panel 112 to select the INPUT COMPLETE button displayed in the vicinity of the bottom edge of the initial information input screen. Step 302 is determined in the affirmative when the radiographer has selected the INPUT COMPLETE button and processing then transitions to step 304.

At step 304 the CPU 113 transmits the data input to the initial information input screen (referred to below as "initial information") to the electronic cassette 40 through the wireless communication unit 119. Then at the next step 306 the exposure conditions are set by transmitting the exposure conditions included in the initial information to the radiation generator 120 through the wireless communication unit 119.

The controller 122 of the radiation generator 120 then performs preparation for exposure according to the received exposure conditions.

At the next step 308, the CPU 113 transmits instruction data instructing the start of exposure to the radiation generator 120 and the electronic cassette 40 through the wireless communication unit 119.

In response the radiation source 121 starts emitting the radiation X with the tube voltage and tube current corresponding to the exposure conditions the radiation generator 120 has received from the console 110. The radiation X emitted from the radiation source 121 reaches the electronic cassette 40 after passing through the patient (imaging subject).

The cassette controller 58 of the electronic cassette 40 receives the instruction data instructing the start of exposure, and remains on standby until the radiation amount detected by the radiation detection pixels 32A reaches a predetermined threshold value or greater that serves as a value for detecting that radiation irradiation has started. The electronic cassette 40 starts radiographic imaging operation when determination is made that the radiation amount detected by the radiation detection pixels 32A has reached the threshold value or greater. The electronic cassette 40 ends the radiographic imaging operation after a specific accumulation duration has elapsed since the start of radiation irradiation, and then transmits the thus obtained image data to the console 110.

At the next step 310, the CPU 113 enters standby until the image data is received from the electronic cassette 40, and at the next step 312, image processing is performed on the received image data to perform various corrections such as shading correction after the missing pixel correction processing described above has been performed.

Then at the next step 314 the CPU 113 stores in the HDD 116 the image data that has been subject to image processing (referred to below as "corrected image data"). Then at the next step 316 the display driver 117 is controlled so as to display a radiographic image expressed by the corrected image data on the display 111, in order for example to perform verification.

At the next step 318 the CPU 113 transmits the corrected image data to the RIS server 150 over the in-hospital network 102, after which the radiographic imaging processing program is ended. The corrected image data transmitted to the RIS server 150 is stored in the database 150A, thereby enabling a medical doctor to read the captured radiographic image and perform diagnostics.

Figure 15:
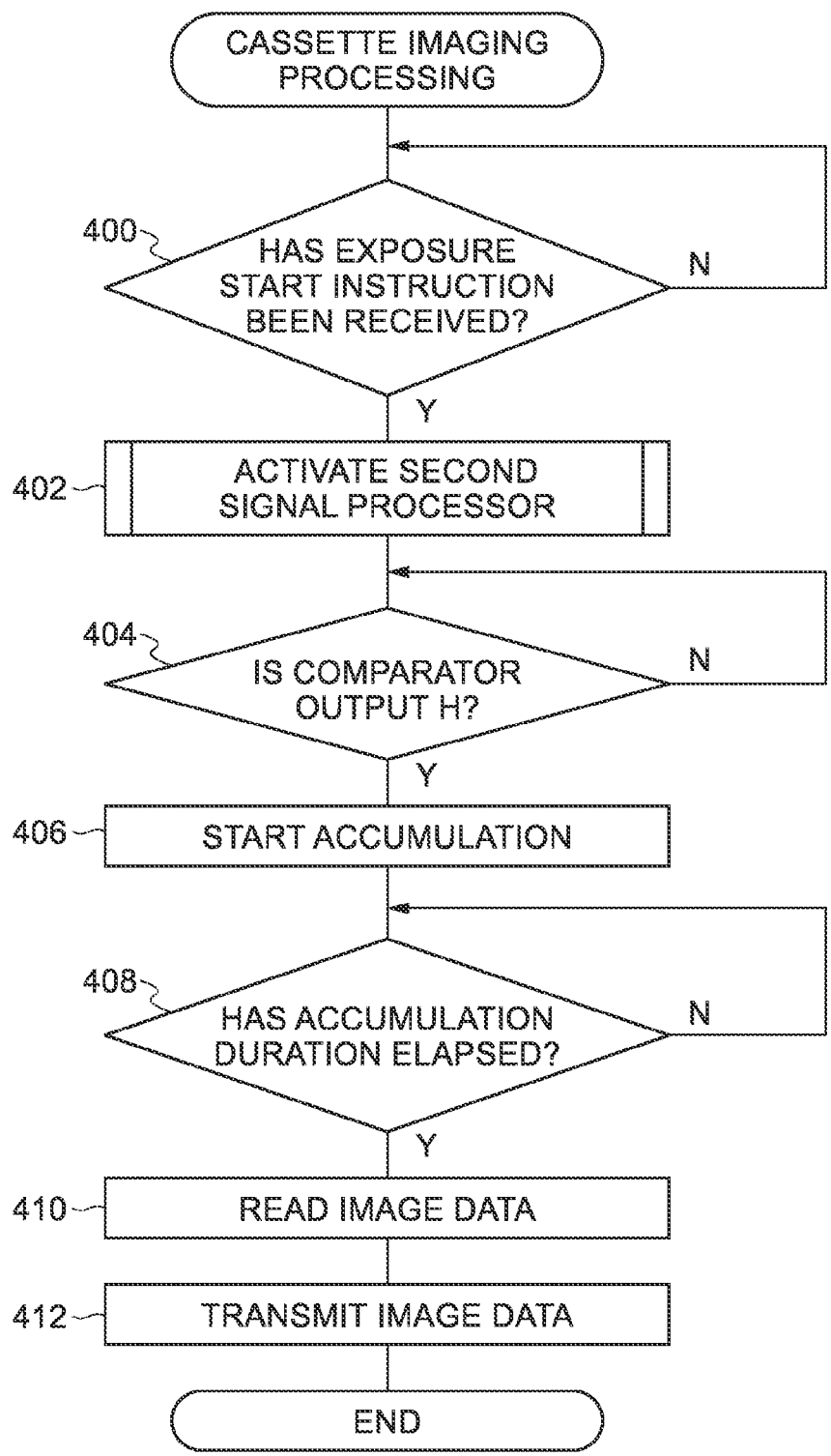
FIG. 15 is a flow chart illustrating a processing flow in a cassette imaging processing program according to an exemplary embodiment of the present invention.

Explanation follows regarding operation of the electronic cassette 40 when the initial information is received from the console 110, with reference to FIG. 15. FIG. 15 is a flow chart illustrating the flow of processing of a cassette imaging processing program executed by the CPU 58A of the cassette controller 58 in the electronic cassette 40 when initial information is received from the console 110. The cassette imaging program is pre-stored in a specific region of the storage unit 58C of the cassette controller 58.

At step 400, the CPU 58A awaits receipt of instruction data instructing exposure start, described above, from the console 110. Processing transitions to step 402 when the CPU 58A has received the instruction data.

At step 402, the CPU 58A supplies to the second signal processor 55 a control signal to activate the second signal processor 55. Each configuration element of the second signal processor 55 is accordingly activated. At this point, since radiation is not being emitted from the radiation source 121, only the noise component due to dark charge accumulated in the sensor portions 13 of each of the radiation detection pixels 32A, and the noise component due to external noise sources present in the direct read lines 38, are read by the second signal processor 55. The charge amplifiers 92, the sample-and-hold circuits 93, the A/D converters 94 and the summation processor 95 of the second signal processor 55 operate in synchronization with each other such that the noise component levels appearing in each of the direct read lines 38 are thereby converted into digital values at a specific sampling cycle and are subjected to summation processing. The sequentially generated summed values from the summation processor 95 are supplied to the noise data generator 96 as noise level sampling values.

Figure 16:
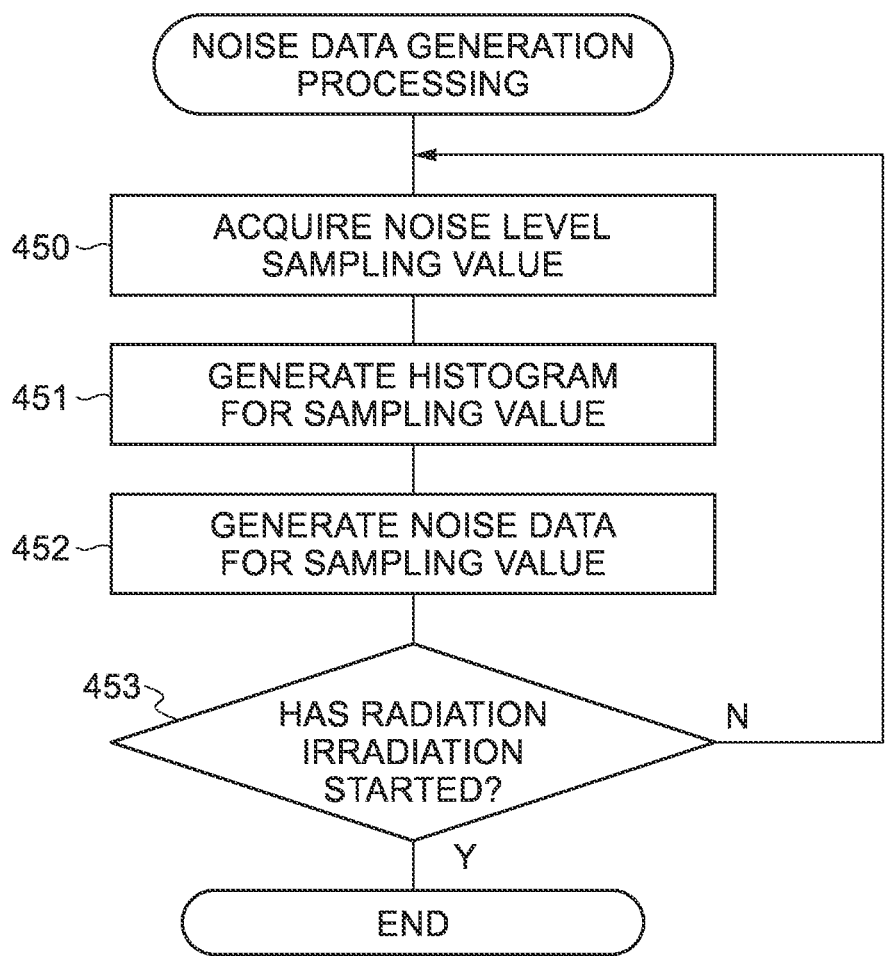
FIG. 16 is a flow chart illustrating a processing flow in a noise data generation processing program according to an exemplary embodiment of the present invention.

The noise data generator 96 executes a noise data generation processing program stored in a storage region within the noise data generator 96 when the second signal processor 55 is activated. FIG. 16 is a flow chart illustrating a flow of processing in such a noise data generation processing program. At step 450, the noise data generator 96 sequentially acquires sampling values of noise level generated in the summation processor 95. At step 451, the noise data generator 96 generates a histogram based on the plural acquired noise level sampling values. At step 452, the noise data generator 96 generates, as noise data, a statistical value such as the maximum value Amax, the minimum value Amin, the average value $\mu$, the variance $\sigma^2$, or the standard deviation $\sigma$ of the plural acquired noise level sampling values. The generated noise data are sequentially supplied to the threshold value controller 97. At step 453, the noise data generator 96 determines whether or not radiation irradiation has started based on the output from the comparator 99. Processing returns to step 450 when the noise data generator 96 determines at step 453 that radiation irradiation has not started, and a new noise level sampling value is acquired and the histogram and the noise data are updated. However, the present routine is ended when at step 453 the noise data generator 96 determines that radiation irradiation has started.

Figure 17:
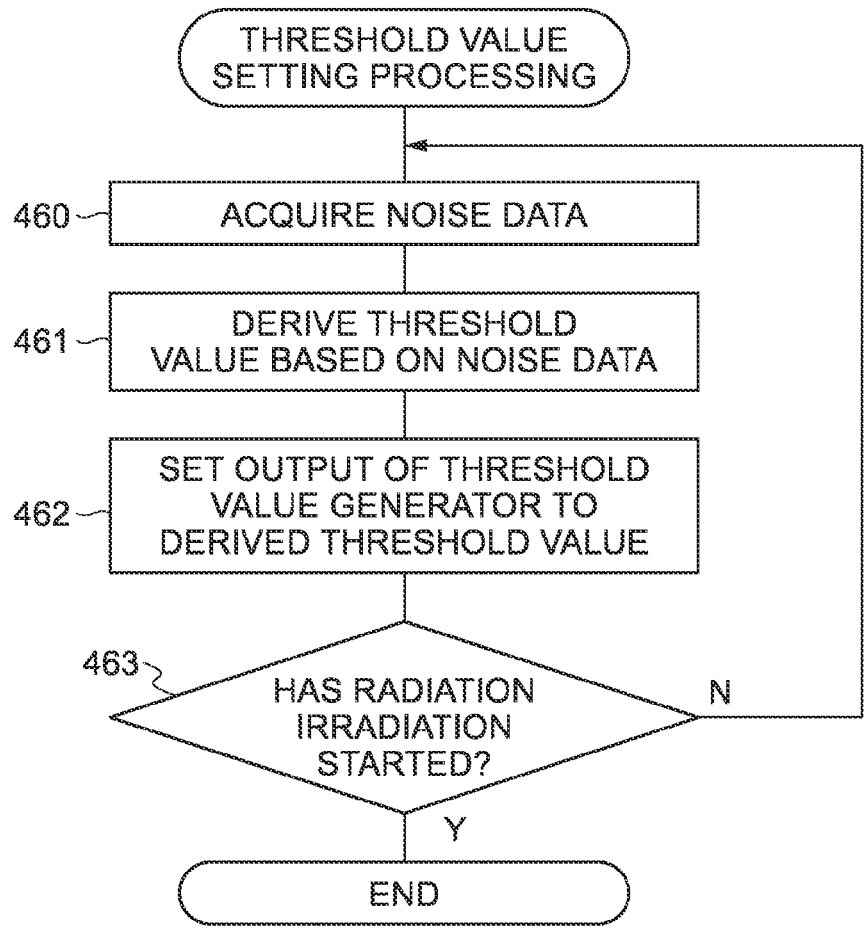
FIG. 17 is a flow chart illustrating a processing flow in a threshold value setting processing program according to an exemplary embodiment of the present invention.

On activation of the second signal processor 55, the threshold value controller 97 executes a threshold value setting processing program stored in a storage region within the threshold value controller 97 itself. FIG. 17 is a flow chart illustrating a flow of processing in such a threshold value setting processing program. At step 460, the threshold value controller 97 acquires the noise data generated by the noise data generator 96. At step 461, the threshold value controller 97 derives a threshold value according to the variation in noise level expressed in the acquired noise data. More specifically, the threshold value controller 97 derives a higher threshold value the greater the amount of variation in noise level expressed by the noise data, thereby lowering the detection sensitivity to radiation irradiation start. In the present exemplary embodiment, the threshold value controller 97 extracts the average value $\mu$ and the standard deviation $\sigma$ from the noise data generated by the noise data generator 96, and derives as the threshold value $\mu+m\sigma$ (where m is a value of 1 or greater). At step 462, the threshold value controller 97 sets an output value of the threshold value generator 98 to the value derived at the previous step 461. The threshold value generator 98 accordingly generates the threshold value derived by the threshold value controller 97 and supplies the generated threshold value to one input of the comparator 99. At step 463, the threshold value controller 97 determines whether or not radiation irradiation has started based on the output of the comparator 99. Processing returns to step 460 when at step 463 the threshold value controller 97 determines that radiation irradiation has not started, and updated noise data is then acquired. However, the present routine is ended when at step 463 the threshold value controller 97 determines that radiation irradiation has started.

The noise data generator 96 thus updates the histogram and noise data each time a new signal value is acquired from the summation processor 95 in the period until radiation irradiation is started. The threshold value controller 97 derives a new threshold value based on the most up-to-date updated noise data, and the threshold value generator 98 generates the threshold value that has been newly derived by the threshold value controller 97. Namely, the threshold value generated by the threshold value generator 98 is controlled to follow fluctuations in the constantly changing noise level values. Such control continues until the detection of radiation irradiation start. Note that configuration may be made such that the noise data generator 96 does not perform unlimited noise level sampling in the period until radiation irradiation is started, and instead generates the histogram and the noise data for each of specific number of times of sampling n. In such cases, the noise data generator 96 may update the histogram and the noise data each time a new sampling value is supplied from the summation processor 95, or may update the histogram and noise data at the point at which n new sampling values have been supplied from the summation processor 95.

Accordingly, at step 402 of the main routine, the threshold value for radiation irradiation start detection is set in a non-irradiation state of radiation from the radiation source 121 by activating the second signal processor 55.

At the next step 404, the CPU 58A remains in standby until the output of the comparator 99 of the second signal processor 55 becomes high level. During this period, the detection operation of radiation irradiation start continues in the second signal processor 55 whilst performing threshold value adjustment corresponding to the variation in the noise level as described above. When radiation is emitted from the radiation source 121, a signal value is input from the summation processor 95 into the comparator 99 with a value greater than the threshold value generated in the threshold value generator 98. The comparator 99 therefore generates a high level output signal and supplies the high level output signal to the CPU 58A of the cassette controller 58. Radiation exposure from the radiation source 121 is treated as having started when the CPU 58A has received the high level output signal from the comparator 99, and processing transitions to step 406. Note that configuration may be made such that in the period until the detection of radiation irradiation start, the CPU 58A supplies control signals to the gate line driver 52 at specific intervals to perform a reset operation in order to discharge dark charge accumulated in the radiographic imaging pixels 32B. On receipt of such a control signal, the gate line driver 52 supplies drive signals to the gate lines 34 in sequence, switching ON the thin film transistors 10 one line at a time. Dark charge accumulated in the radiographic imaging pixels 32B is thereby discharged into the signal lines 36 to reset each of the pixels.

At the next step 406, the CPU 58A supplies a control signal to the gate line driver 52 to switch all of the thin film transistors 10 to an OFF state. The radiographic imaging pixels 32B accordingly start to accumulate charge generated according to radiation irradiation, transitioning to a radiographic imaging operation.

At the next step 408, the CPU 58A determines whether or not a specific accumulation duration has elapsed since transition to the accumulation operation. Processing transitions to step 410 when the CPU 58A has determined that the specific accumulation duration has elapsed since transitioning to the accumulation operation.

At the next step 410, the CPU 58A supplies a control signal to the gate line driver 52, thereby causing ON signals to be output in sequence one line at a time from the gate line driver 52 to each of the gate lines 34, and switching each of the thin film transistors 10 connected to each of the gate lines 340N in sequence one line at a time. The charges accumulated in the capacitors 9 of each of the radiographic imaging pixels 32B are accordingly read into each of the signal lines 36, are converted into digital image data in the first signal processor 54, and the digital image data is stored in the image memory 56.

At the next step 412, the CPU 58A reads the image data stored in the image memory 56 and the present cassette imaging processing program is ended after transmitting the read image data to the console 110 through the wireless communication unit 60.

In the electronic cassette 40 of the present exemplary embodiment, as shown in FIG. 8, the radiation detector 20 is disposed such that radiation X is irradiated from the TFT substrate 30 side of the electronic cassette 40.

Figure 18:
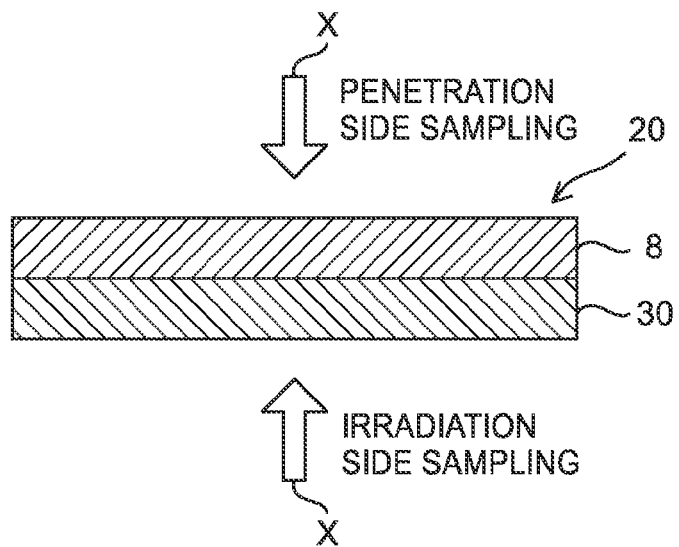
FIG. 18 is a side on cross-section to explain an irradiation side sampling method and a penetration side sampling method of radiographic imaging.

In cases using what is referred to as a Penetration Side Sampling (PSS) method in which the radiation detector 20 is irradiated with radiation from the side on which the scintillator 8 is formed, as shown in FIG. 18, and radiographic images are read by the TFT substrate 30 provided on the opposite side to the radiation incident face, light is emitted with higher intensity from the top face side of the scintillator 8 in FIG. 18 (the opposite side to the face joined to the TFT substrate 30). However, in cases using what is referred to as an Irradiation Side Sampling (ISS) method in which radiation is irradiated from the TFT substrate 30 side and radiographic images are read by the TFT substrate 30 provided on the radiation incident face side, radiation that has passed through the TFT substrate 30 is incident to the scintillator 8 and light is emitted with higher intensity from the side of the scintillator 8 of the face joined to the TFT substrate 30. Each of the sensor portions 13 provided to the TFT substrate 30 generates charge according to the light generated in the scintillator 8. The radiographic images captured are accordingly of higher resolution when an ISS method is employed than when a PSS method is employed since the light emission position of the scintillator 8 is closer to the TFT substrate 30.

The radiation detector 20 is also configured with the photoelectric conversion layer 4 formed from an organic photoelectric conversion material and so radiation is barely absorbed by the photoelectric conversion layer 4. The radiation detector 20 of the present exemplary embodiment is accordingly capable of suppressing deterioration in sensitivity to radiation, since the amount of radiation absorbed by the photoelectric conversion layer 4 is smaller even when radiation passes through the TFT substrate 30 due to employing an ISS method. In an ISS method the radiation has passed through the TFT substrate 30 to reach the scintillator 8. However application may be made to an ISS method when the photoelectric conversion layer 4 of the TFT substrate 30 is thus configured from an organic photoelectric conversion material, since there is hardly any radiation absorption in the photoelectric conversion layer 4 and radiation attenuation can be suppressed to a small amount.

It is also possible to form both the amorphous oxide configuring the active layer 17 of the thin film transistors 10 and the organic photoelectric conversion material configuring the photoelectric conversion layer 4 using film forming at low temperature. The substrate 1 can accordingly be formed from plastic resin with aramid and/or bionanofibers, having low absorptivity to radiation. Since the amount of radiation absorbed by the thus formed substrate 1 is small, sensitivity to radiation can be suppressed from deteriorating even when radiation passes through the TFT substrate 30 due to employing an ISS method.

According to the present exemplary embodiment, as shown in FIG. 8, the radiation detector 20 is attached inside the housing 41 to the top plate 41B so that the TFT substrate 30 is on the top plate 41B side. Moreover, the top plate 41B of the housing 41 can be formed thinner in cases in which the substrate 1 is formed with high rigidity from a plastic resin with aramid and/or bionanofibers, since the rigidity of the radiation detector 20 itself is high. The radiation detector 20 is also not easily damaged in cases in which the substrate 1 is formed with high rigidity from a plastic resin with aramid and/or bionanofibers, even when the imaging region 41A incurs an impact since the radiation detector 20 itself is flexible.

As made clear in the above explanation, the electronic cassette 40 according to the first exemplary embodiment of the present invention detects radiation irradiation start when the signal level of an electric signal according to the charge amount generated in the sensor portions 13 of the radiation detection pixels 32A becomes greater than the threshold value generated by the threshold value generator 98 of the second signal processor 55. The second signal processor 55 performs noise level sampling of noise incorporated in the detection system, for example the direct read lines 38, by performing read processing on the charges from the radiation detection pixels 32A in a non-irradiation state of radiation. The noise data generator 96 generates as noise data a statistical value such as the maximum value Amax, the minimum value Amin, the average value $\mu$, the variance $\sigma^2$ or the standard deviation $\sigma$ of the noise level from the noise level sampling values. The threshold value controller 97 sets a higher threshold value the greater the amount of variation in the noise level expressed in the noise data, reducing the detection sensitivity to radiation irradiation start. Setting a higher threshold values acts in the direction to make false detection of radiation irradiation start due to noise less liable to occur.

In the electronic cassette 40 of the present exemplary embodiment, the detection sensitivity to radiation irradiation start is accordingly lowered the greater the variation in actual measured noise level. Namely, although it is foreseen that the level of incorporated noise will fluctuate greatly in a noisy environment affected by external noise sources such as electromagnetic waves and vibration, by setting the threshold value according to variation in the actual measured noise level, it is possible to effectively reduce false detection not only due to for example low or intermediate level noise that occurs with relatively high frequency, but also due to high level noise that occurs with relatively low frequency. Therefore, according to the electronic cassette 40 of the present exemplary embodiment, the false detection of radiation irradiation start can be reduced even in noisy environments that are affected by external noise.

Note that in the above exemplary embodiment, an example has been given of a case in which the threshold value controller 97 derives $\mu+m\sigma$ as the threshold value according to variation in the noise level, however there is no limitation thereto. The threshold value controller 97 may derive threshold values as described below.

The noise data generator 96 supplies the threshold value controller 97 with a maximum value Amax1 for the first n sampling values and a maximum value Amax 2 (Amax1<Amax2) for the following n sampling values as noise data. The threshold value controller 97 employs a difference value D between Amax1 and Amax2 (D=Amax2−Amax1) as an indicator value of the variation in the noise level, and may for example derive as a threshold value Amax2+k·|D|. Here, k is a value of 1 or greater. False detection for the maximum level noise can accordingly be greatly reduced by setting as the threshold value the maximum value Amax2 of the actual measured noise level to which is added k·|D| corresponding to the noise level variation.

The threshold value controller 97 may also derive the threshold value by referencing a reference table of variation indicator values, such as the standard deviation σ or the variance $\sigma^2$ of the of noise level, associated with threshold values. In such cases, the reference table is constructed such that the greater the value of the standard deviation σ or the variance $\sigma^2$, the higher the threshold value derived. The reference table is pre-stored in the storage region of the threshold value controller 97.

Second Exemplary Embodiment

Explanation follows regarding an electronic cassette according to a second exemplary embodiment of the present invention. The electronic cassette 40 of the first exemplary embodiment described above adjusts the detection sensitivity to radiation irradiation start by adjusting the threshold value used to determine radiation irradiation start according to the degree of variation in the noise level expressed in the noise data. In contrast thereto, the electronic cassette of the second exemplary embodiment adjusts the detection sensitivity to radiation irradiation start by adjusting the gain of a charge amplifier according to the degree of variation in the noise level expressed by the noise data.

Figure 19:
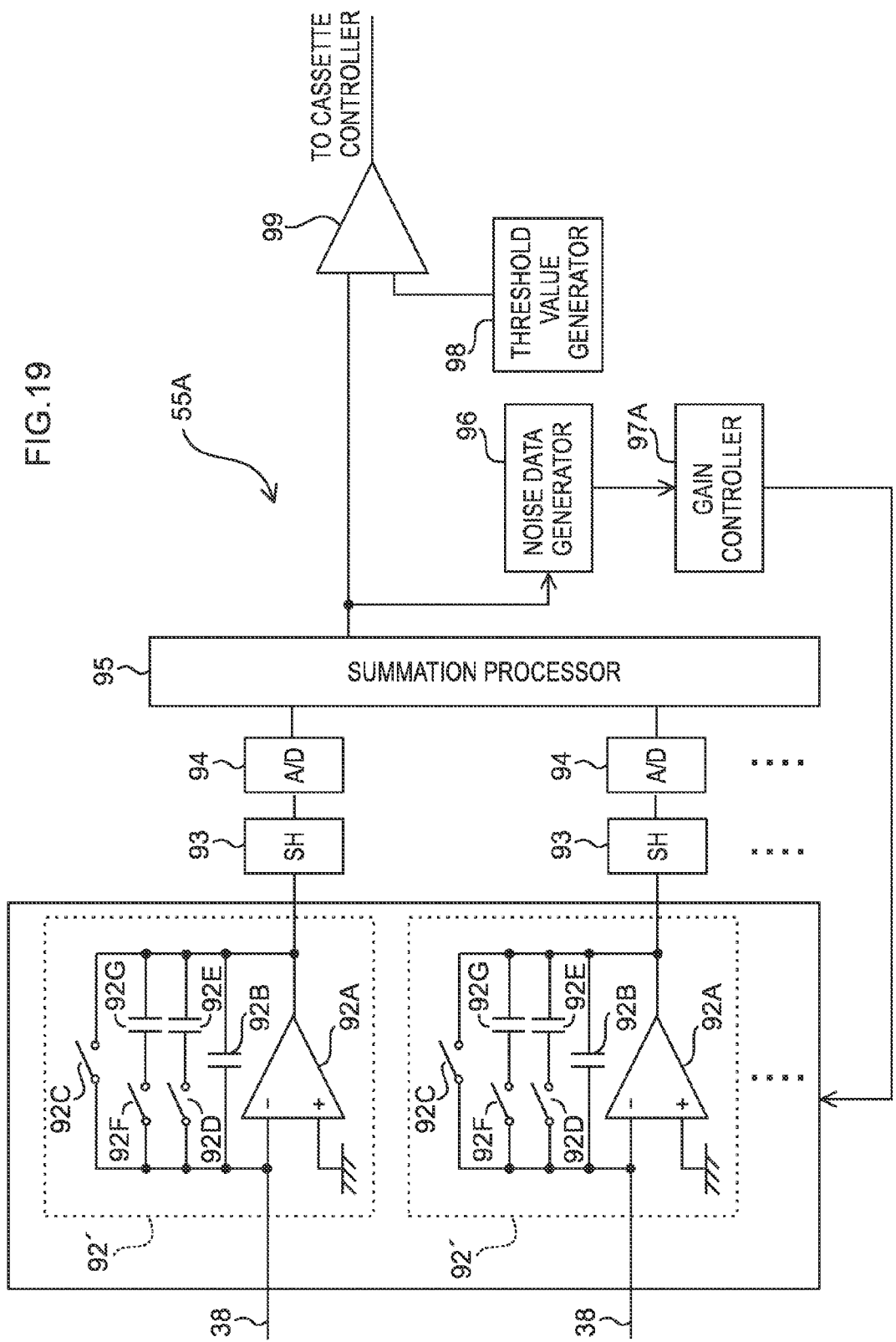
FIG. 19 is a diagram illustrating a configuration of a second signal processor according to a second exemplary embodiment of the present invention.

FIG. 19 illustrates a configuration of a second signal processor 55A according to the second exemplary embodiment of the present invention. In the following, explanation is given regarding portions of the second signal processor 55A of the present exemplary embodiment that differ from the second signal processor 55 according to the first exemplary embodiment. Note that portions of the second signal processor 55A common to the second signal processor 55 of the first exemplary embodiment described above are allocated the same reference numerals and explanation thereof is omitted. Moreover, configuration portions other than the second signal processor 55A are similar to those of the first exemplary embodiment and so further explanation thereof is omitted.

The second signal processor 55A includes gain adjustable charge amplifiers 92'. In order to enable gain adjustment, the charge amplifiers 92' are each configured with a series circuit including a switch 92D and a capacitor 92E and a series circuit including a switch 92F and a capacitor 92G, with these two circuits connected in parallel to the capacitor 92B. The switch 92D and the switch 92F are switched ON and OFF by a control signal supplied from a gain controller 97A. The compound capacity connected between the input and output terminals of an operational amplifier 92A is varied by switching the switch 92D and the switch 92F ON and OFF, thereby varying the gain of the charge amplifier 92'. More specifically, the gain is varied so as to become smaller the greater the compound capacity (namely, as the number of connected capacitors increases). In the present exemplary embodiment an example is given of a case in which two series circuits each configured by a switch and a capacitor are provided, with three steps of gain adjustment performed. However the number of series circuits configured by a switch and a capacitor may be increased or reduced as appropriate according to the gain adjustment range and/or the number of steps of gain adjustment.

The gain controller 97A controls to switch the switches 92D and 92F ON or OFF so as to reduce the gain of each of the charge amplifiers 92' the greater the variation in the noise level expressed in the noise data supplied from the noise data generator 96. The gain controller 97A acquires for example the standard deviation σ from the noise data supplied from the noise data generator 96 as an indicator value of variation in the noise level. The gain controller 97A includes a reference table 500 of ranges of standard deviation σ associated with ON and OFF states of the switches 92D and 92F configuring the charge amplifiers 92', such as that shown in FIG. 20, stored in a storage region provided to the gain controller 97A itself. In the reference table 500, the standard deviations σ are associated with drive states of the switches 92D and 92F such that the gain of the charge amplifiers 92' becomes smaller greater the value of the standard deviation σ. The gain controller 97A derives the drive states of the switches 92D and 92F associated with the standard deviation σ contained in the noise data supplied from the noise data generator 96 by searching the reference table 500. The gain controller 97A then supplies control signals to the charge amplifiers 92' to switch the switches 92D and 92F to the derived drive states, thereby controlling the gain of the charge amplifiers 92'.

Note that the noise data generator 96 sequentially updates a histogram and the noise data similarly to in the first exemplary embodiment. The gain controller 97A derives a new gain setting according to the updated noise data when the noise data is updated. Namely, the gain controller 97A varies the gain setting adaptively according to noise generation conditions by deriving the gain setting based on the most up-to-date noise data.

Similarly to in the first exemplary embodiment, the second signal processor 55A of the present exemplary embodiment performs noise level sampling of noise that has entered the detection system, for example the direct read lines 38, by performing read processing on charges from the radiation detection pixels 32A in a non-irradiation state of radiation. The noise data generator 96 generates as noise data a statistical value such as a maximum value Amax, a minimum value Amin, an average value μ, a variance $\sigma^2$ or the standard deviation σ of the noise level from the noise level sampling values. The gain controller 97A reduces the detection sensitivity to radiation irradiation start the greater the variation in noise level expressed in the noise data, by controlling so as to reduce the gain of the charge amplifiers 92'. The charge amplifiers 92' also amplify the noise level incorporated into the direct read lines 38 along with the signal charges flowing in the direct read lines 38. Accordingly, by reducing the gain of the charge amplifiers 92', the noise level input into the comparator 99 can also be reduced, thereby acting in the direction so as to make false detection of radiation irradiation start caused by noise less liable to occur Similarly to the electronic cassette 40 of the first exemplary embodiment, in the electronic cassette of the present exemplary embodiment the detection sensitivity to radiation irradiation start is reduced the greater the amount of variation in noise level sampling values. Namely, although it is foreseen that the level of incorporated noise will fluctuate greatly in a noisy environment affected by external noise sources such as electromagnetic waves and vibration, by setting the gain of the charge amplifiers 92' according to the amount of variation in the actual measured noise level, it is possible to effectively reduce false detection due to high level noise that occurs with relatively low frequency. Therefore, according to the electronic cassette of the present exemplary embodiment, the false detection of radiation irradiation start can be reduced even in noisy environments that are affected by external noise.

Note that in the present exemplary embodiment, an example has been given of a case in which the gain of the charge amplifiers 92' is set according to the standard deviation σ of the noise level. However, the gain of the charge amplifiers 92' may also be set according to a variation indicator value other than the standard deviation σ (for example the variance $σ^2$ or the difference between the maximum value Amax and the minimum value Amin).

Third Exemplary Embodiment

Explanation follows regarding an electronic cassette of a third exemplary embodiment of the present invention. The electronic cassette 40 according to the first exemplary embodiment described above adjusts the detection sensitivity to radiation irradiation start by adjusting the threshold value used to determine radiation irradiation start according to the degree of variation in the noise level expressed in the noise data. However, the electronic cassette of the third exemplary embodiment adjusts the detection sensitivity to radiation irradiation start by adjusting the charge accumulation duration in the charge amplifiers 92 according to the degree of noise level variation expressed in the noise data.

Figure 21:
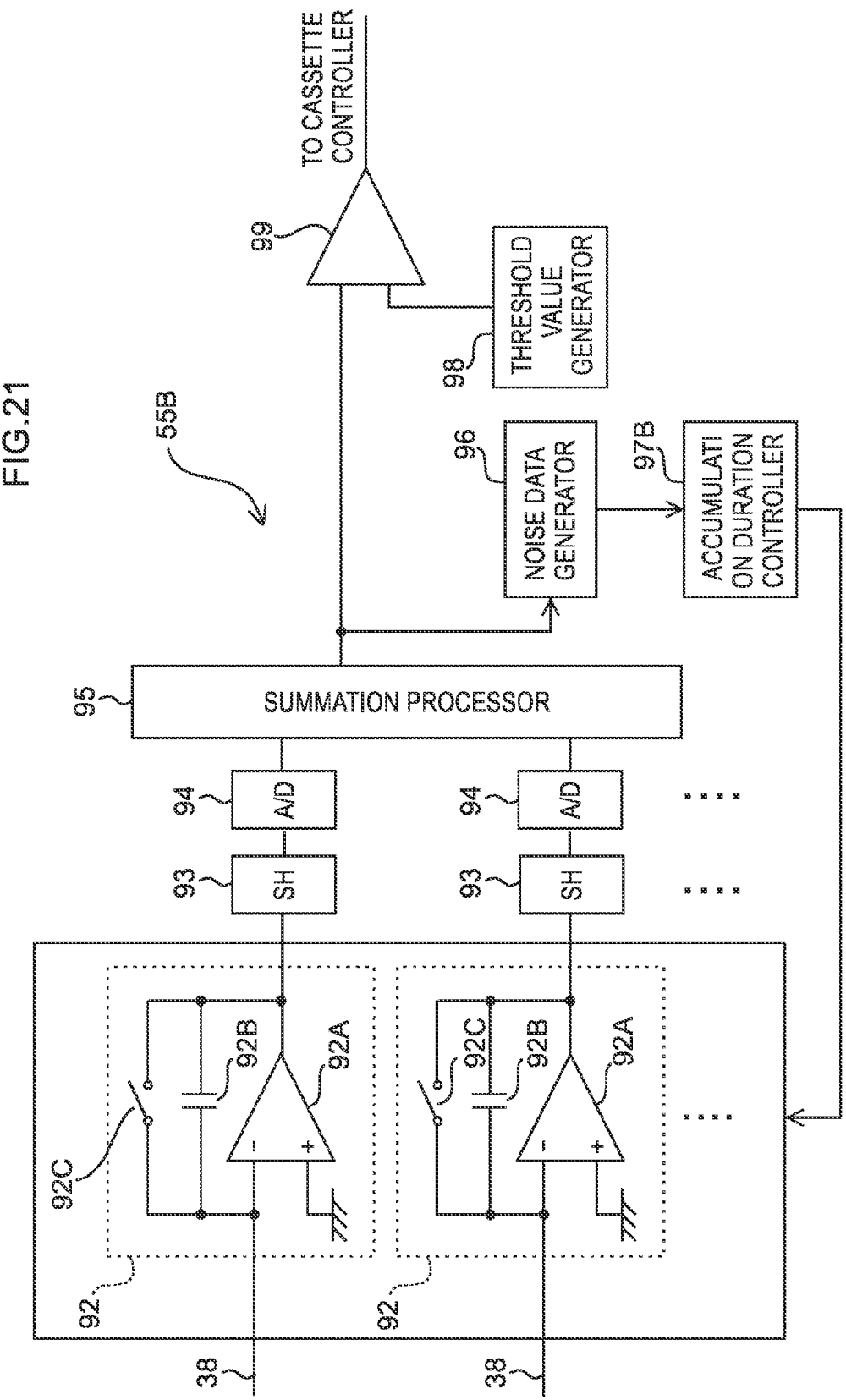
FIG. 21 is a diagram illustrating a configuration of a second signal processor according to a third exemplary embodiment of the present invention.

FIG. 21 illustrates a configuration of a second signal processor 55B according to the third exemplary embodiment of the present invention. In the following, explanation is given regarding portions that differ between the second signal processor 55B according to the present exemplary embodiment and the second signal processor 55 of the first exemplary embodiment. Note that portions of the second signal processor 55B common to the second signal processor 55 of the first exemplary embodiment are allocated the same reference numerals and explanation thereof is omitted. Moreover, configuration portions other than the second signal processor 55B are similar to those of the first exemplary embodiment and so further explanation thereof is omitted.

An accumulation duration controller 97B controls a drive timing of a reset switch 92C such that the charge accumulation duration of charge amplifiers 92 becomes longer the greater the amount of noise level variation expressed in noise data supplied from the noise data generator 96. The accumulation duration controller 97B acquires for example a standard deviation σ as an indicator value of noise level variation from the noise data supplied from the noise data generator 96. The accumulation duration controller 97B includes a reference table 501 of ranges of standard deviation σ associated with charge accumulation durations for the charge amplifiers 92, such as shown in FIG. 22, stored in a storage region of the accumulation duration controller 97B itself. In the reference table 501, the standard deviations σ are associated with charge accumulation durations such that the charge accumulation duration of the charge amplifiers 92 becomes longer the greater the value of the standard deviation σ. The accumulation duration controller 97B derives the charge accumulation duration corresponding to the standard deviation σ included in the noise data supplied from the noise data generator 96 by searching the reference table 501. The accumulation duration controller 97B controls the charge accumulation duration (namely, the reset cycle) by supplying control signals to the charge amplifiers 92 and controlling the ON/OFF timing of the reset switches 92C to achieve the derived charge accumulation duration.

Note that the noise data generator 96 sequentially updates a histogram and the noise data similarly to in the first exemplary embodiment. In noise data updating the accumulation duration controller 97B derives a new charge accumulation duration according to the updated noise data. Namely, the accumulation duration controller 97B varies the charge accumulation duration adaptively according to noise generation conditions by deriving the charge accumulation duration based on the most up-to-date noise data.

Similarly to in the first exemplary embodiment, the second signal processor 55B of the present exemplary embodiment performs noise level sampling of noise that has entered the detection system, for example the direct read lines 38, by performing read processing on charge from the radiation detection pixels 32A in a non-irradiation state of radiation. The noise data generator 96 generates as noise data a statistical value such as a maximum value Amax, a minimum value Amin, an average value μ, the variance $σ^2$, or the standard deviation σ of the noise level from the noise level sampling values. The accumulation duration controller 97B controls so as to raise the detection sensitivity to radiation irradiation start by increasing the charge accumulation duration of the charge amplifiers 92 the greater the amount of noise level variation expressed in the noise data.

Each of the charge amplifiers 92 generates an electric signal having a signal level corresponding to the charge amount accumulated in the capacitor 92B. Accordingly, the longer the charge accumulation duration, the greater the charge amount accumulated in the capacitors 92B, and the higher the signal level of the electric signals output from the charge amplifiers 92. Namely, the signal level based on the signal charge generated in the radiation detection pixels 32A can be increased with respect to the noise level the longer the charge accumulation duration of the charge amplifier 92. In other words, the longer the charge accumulation duration of the charge amplifiers 92, the higher the signal-to-noise ratio is raised, and the higher the detection sensitivity to radiation irradiation start is raised. The signal level with respect to the noise level can accordingly be raised by increasing the charge accumulation duration of the charge amplifiers 92, thereby acting in the direction to make false detection of radiation irradiation start due to noise less liable to occur.

In the electronic cassette of the present exemplary embodiment, the detection sensitivity to radiation irradiation start can accordingly be set higher by increasing the charge accumulation duration of the charge amplifiers 92 the greater the amount of variation in the noise level sampling values. Namely, although it is foreseen that the level of incorporated noise will fluctuate greatly in a noisy environment affected by external noise sources such as electromagnetic waves and vibration, by setting the charge accumulation duration of the charge amplifiers 92 according to the amount of variation in the actual measured noise level, it is possible to effectively reduce false detection due to high level noise that occurs with relatively low frequency. Therefore, according to the electronic cassette of the present exemplary embodiment, the false detection of radiation irradiation start can be reduced even in noisy environments that are affected by external noise.

Note that in the present exemplary embodiment, an example has been given of a case in which the charge accumulation duration of the charge amplifiers 92 is set according to the standard deviation σ of the noise level. However, the charge accumulation duration of the charge amplifiers 92 may be set according to a variation indicator value other than the standard deviation σ (for example the variance $σ^2$ or the difference between the maximum value Amax and the minimum value Amin).

Figure 23:
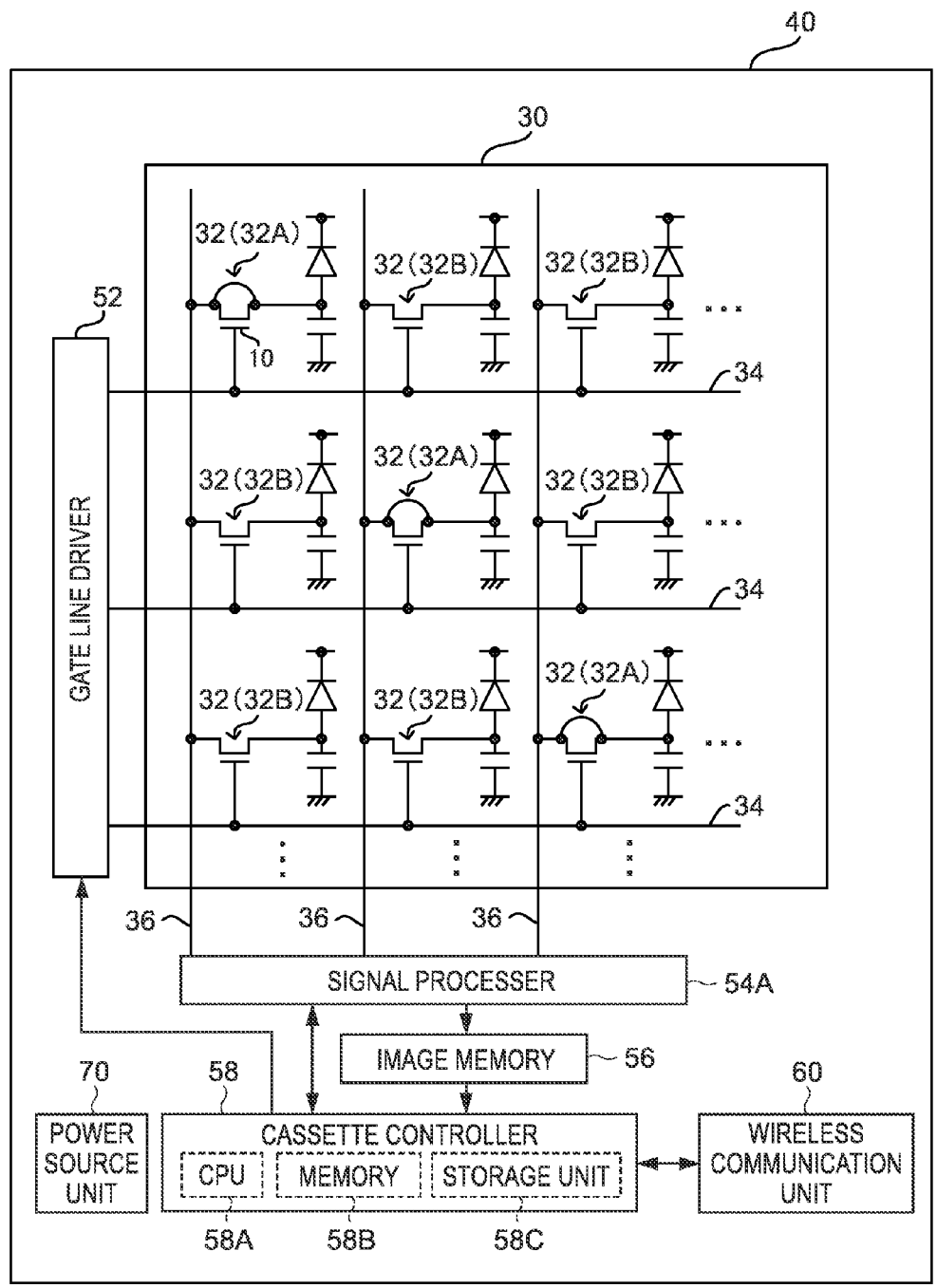
FIG. 23 is a diagram illustrating a configuration of an electronic cassette according to another exemplary embodiment of the present invention.

Moreover, in each of the exemplary embodiments described above, examples have been given in which pixel data for radiation detection obtained from the radiation detection pixels 32A is transmitted to the second signal processors 55, 55A, 55B through the direct read lines 38, and radiation irradiation start is detected by the second signal processors 55, 55A, 55B, however there is no limitation to such a configuration. For example as shown in FIG. 23, configuration may be made wherein the sources and drains of the thin film transistors 10 are shorted, and pixel data obtained from the radiation detection pixels 32A is thereby read into the signal lines 36. In cases in which such a configuration is adopted, the function of the first signal processor 54 in each of the above exemplary embodiments (the function of reading pixel data obtained from the radiographic imaging pixels 32B and generating a radiographic image) and the function of the second signal processor 55, 55A, 55B (the function of detecting radiation irradiation start, the function of generating noise data, and the function of setting detection sensitivity according to the noise data) are unified in a signal processor 54A.

In each of the exemplary embodiments described above, explanation has been given of cases in which some of the pixels 32 provided to the radiation detector 20 are employed for the radiation detection pixels 32A, however the present invention is not limited thereto. For example, the radiation detector 20 may have a stacked configuration with the radiation detection pixels 32A in a separate layer to the pixels 32. In such cases, the quality of radiographic images can be raised in comparison to the above exemplary embodiments since there are no missing pixels.

Figure 24A:
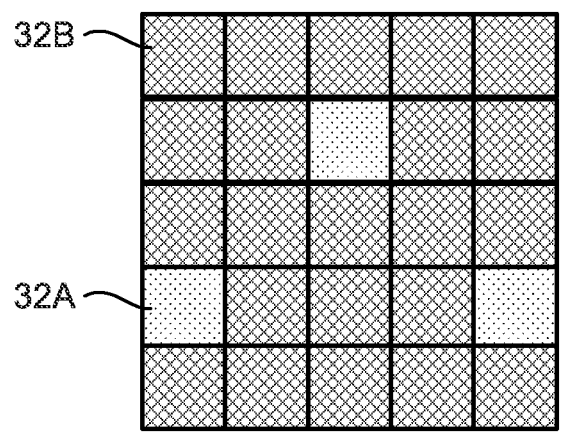
FIG. 24A and FIG. 24B are plan views illustrating disposal of radiation detection pixels according to other exemplary embodiments of the present invention.
Figure 24B:
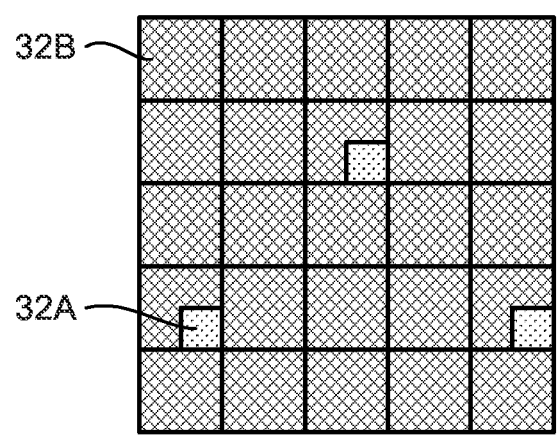

Moreover, in the above exemplary embodiments explanation has been given of cases in which some of the radiographic imaging pixels 32B are applied as the radiation detection pixels 32A, as shown in the example in FIG. 24A, however the present invention is not limited thereto and the radiation detection pixels 32A may be provided in gaps between the radiographic imaging pixels 32B, for example as shown in the example in FIG. 24B. In such cases, the sensitivity of the radiographic imaging pixels 32B provided at positions corresponding to the radiation detection pixels 32A decreases since the surface area of these radiographic imaging pixels 32B decreases, however the quality of radiographic images can be increased since these pixels can also be used for radiographic image detection.

The sensors for detecting radiation do not necessarily have to be applied to the pixels of the radiation detector 20, and configuration may be made such that radiation irradiation start is detected by designated radiation detection sensors that generate charge on irradiation with radiation, provided for example between each row of pixels in the radiation detector 20, or at predetermined positions in peripheral positions. In such cases, such sensors do not necessarily have to be provided to the radiation detector 20, and may be disposed as a separate body to the radiation detector 20.

In the above exemplary embodiments, explanation has been given of cases in which the radiation detection pixels 32A and the radiographic imaging pixels 32B are provided separately to one another, however the present invention is not limited thereto. Configuration may be made wherein the radiographic imaging pixels 32B are applied as sensors that determine whether or not radiation has been detected, without providing the radiation detection pixels 32A. Namely, configuration may be made with the sensors that determine whether or not radiation has been detected being common to the radiographic imaging pixels 32B. In such cases, the present invention can be achieved simply, without the need to provide extra sensors.

In the above exemplary embodiments, explanation has been given of cases in which the sensor portions 13 are configured including an organic photoelectric conversion material that generates charge upon receiving light generated by the scintillator 8. The present invention is not limited thereto, and configuration may be made wherein the sensor portions 13 do not include an organic photoelectric conversion material. For example, the sensor portions 13 may employ a semiconductor such as amorphous selenium, in a configuration wherein radiation is converted directly into charge.

In the above exemplary embodiments, explanation has been given of cases in which the case 42 that houses the cassette controller 58 and the power source unit 70 is disposed inside the housing 41 of the electronic cassette 40 so as not to overlap with the radiation detector 20, however there is no limitation thereto. The radiation detector 20 may for example be disposed so as to overlap with the cassette controller 58 and/or the power source unit 70.

In the above exemplary embodiments, explanation has been given of cases in which wireless communication is performed between the electronic cassette 40 and the console 110, and between the radiation generator 120 and the console 110, however the present invention is not limited thereto, and wired communication may be performed between the electronic cassette 40 and the console 110 and/or between the radiation generator 120 and the console 110.

In the above exemplary embodiments, explanation has been given of cases in which X-rays are applied as the radiation, however the present invention is not limited thereto and other radiation such as gamma rays may be applied as the radiation.

Other configurations of the RIS 100 (see FIG. 1), the radiographic imaging room 180 (see FIG. 2), the electronic cassette 40 (see FIG. 3 to FIG. 8) and the imaging systems 104 (see FIG. 9) described in the above exemplary embodiments are merely examples thereof. Obviously, for example, unnecessary portions may be omitted, new portions added, and connection states changed within a scope not departing from the spirit of the present invention.

Moreover, the flow of processing in each of the programs described in the above exemplary embodiments (see FIG. 13, FIG. 15) are also merely examples thereof, and obviously unnecessary steps may be omitted, new steps added, and processing sequences varied within a scope not departing from the spirit of the present invention.

Each of the controls for adjusting the detection sensitivity in the detection of radiation irradiation start illustrated in each of the above exemplary embodiments may be combined as appropriate. For example, the control for adjusting the threshold value described in the first exemplary embodiment may be implemented in combination with the control for adjusting the gain of the charge amplifiers 92 described in the second exemplary embodiment.

Note that in the above exemplary embodiments, explanation has been given regarding cases in which the detection sensitivity is controlled according to the degree of noise level variation, however detection algorithms may also be varied.

What is claimed is:

1. A method of performing radiographic imaging comprising:
    generating an output signal according to an irradiated amount of irradiated radiation using a sensor portion;
    using a detector to detect, based on the output signal, a radiation irradiation start of radiation irradiated from a radiation source during capture of a radiographic image;
    generating noise data with a noise data generator that, based on an output signal from the sensor portion in a non-irradiation state of radiation from the radiation source, generates noise data relating to noise incorporated in the output signal;

using a controller to controls detection sensitivity to radiation irradiation start in the detector according to a degree of variation in noise level expressed by the noise data; and, capturing the radiographic image with an imaging unit after radiation irradiation start has been detected by the detector, wherein:

the controller lowers detection sensitivity to radiation irradiation start in the detector the greater the variation in the noise level expressed by the noise data;

the detector includes an amplifier circuit that amplifies the output signal; and, the controller lowers detection sensitivity to radiation irradiation start by the detector by reducing the gain of the amplification circuit the greater the variation in the noise level expressed by the noise data.

2. The radiographic imaging method of claim 1, wherein the noise data generator sequentially updates the noise data based on the output signal sequentially supplied from the sensor portion; and the controller derives the gain based on the most up-to-date noise data.

3. A method of performing radiographic imaging comprising:

generating an output signal according to an irradiated amount of irradiated radiation using a sensor portion;

a detector to detect based on the output signal, a radiation irradiation start of radiation irradiated from a radiation source during capture of a radiographic image;

generating noise data with a noise data generator that, based on an output signal from the sensor portion in a non-irradiation state of radiation from the radiation source, generates noise data relating to noise incorporated in the output signal;

using a controller to control detection sensitivity to radiation irradiation start in the detector according to a degree of variation in noise level expressed by the noise data; and, capturing the radiographic image with an imaging unit after radiation irradiation start has been detected by the detector, wherein:

the detector includes a charge amplifier that includes a capacitor that accumulates charge output as the output signal from the sensor portion, and that generates an electric signal according to a charge amount accumulated in the capacitor; and, the controller makes a charge accumulation duration of the capacitor longer the greater the noise level variation expressed by the noise data.

4. The radiographic imaging method of claim 3, wherein the noise data generator sequentially updates the noise data based on the output signal sequentially supplied from the sensor portion; and the controller derives the charge accumulation duration based on the most up-to-date noise data.

5. A method of performing radiographic imaging comprising:

generating an output signal according to an irradiated amount of irradiated radiation using a sensor portion;

using a detector to detect, based on the output signal, a radiation irradiation start of radiation irradiated from a radiation source during capture of a radiographic image;

generating noise data with a noise data generator that, based on an output signal from the sensor portion in a non-irradiation state of radiation from the radiation source, generates noise data relating to noise incorporated in the output signal;

using a controller to control detection sensitivity to radiation irradiation start in the detector according to a degree of variation in noise level expressed by the noise data; and, capturing the radiographic image with an imaging unit after radiation irradiation start has been detected by the detector, wherein:

the noise data generator generates a histogram based on the plurality of sampling values.

* * * * *